US012746324B2

(12) United States Patent
Hindmarsh et al.

(10) Patent No.: US 12,746,324 B2
(45) Date of Patent: Sep. 29, 2026

(54) VACUUM THERAPY DEVICES AND METHODS

(71) Applicant: Cambridge University Hospitals NHS Foundation Trust, Cambridge (GB)

(72) Inventors: Andrew Hindmarsh, Cambridge (GB); Sean Licence, Cambridge (GB); Adam Farrow, Cambridge (GB)

(73) Assignee: Cambridge University Hospitals NHS Foundation Trust, Cambridge (GB)

( * ) Notice: Subject to any disclaimer, the term of this patent is extended or adjusted under 35 U.S.C. 154(b) by 608 days.

(21) Appl. No.: 18/262,414

(22) PCT Filed: Jan. 24, 2022

(86) PCT No.: PCT/GB2022/050183
§ 371 (c)(1),
(2) Date: Jul. 21, 2023

(87) PCT Pub. No.: WO2022/157513
PCT Pub. Date: Jul. 28, 2022

(65) Prior Publication Data

US 2024/0115793 A1 Apr. 11, 2024

(30) Foreign Application Priority Data

Jan. 22, 2021 (GB) ...................................... 2100885

(51) Int. Cl.
*A61M 1/00* (2006.01)

(52) U.S. Cl.
CPC ....... *A61M 1/87* (2021.05); *A61M 2205/0222* (2013.01)

(58) Field of Classification Search
CPC ........................ A61M 1/87; A61M 2205/0222
See application file for complete search history.

(56) References Cited

U.S. PATENT DOCUMENTS

2010/0168688 A1 7/2010 Santora et al.
2019/0117857 A1* 4/2019 Hindmarsh ........... A61M 27/00
(Continued)

FOREIGN PATENT DOCUMENTS

EP 2 370 037 B1 5/2019
WO WO 2010/063467 A1 6/2010
(Continued)

OTHER PUBLICATIONS

GB2100885.9 Examination Report dated Oct. 23, 2023.
(Continued)

*Primary Examiner* — Dung T Ulsh
(74) *Attorney, Agent, or Firm* — Woodard Emhardt Henry Reeves & Wagner LLP

(57) ABSTRACT

A vacuum therapy device for treatment of a defect internal of a human or animal body, the device comprising: a porous medium for treatment of the defect; a catheter having a proximal end and a distal end, wherein the catheter is configured to be inserted into the body to enable deployment of the porous medium through an opening at the distal end for treatment of the defect; and a suction element within the catheter, the suction element comprising a suction tube connected to the porous medium to provide suction thereat; wherein the porous medium is movable between: (i) a proximal position in which a majority of the porous medium is inside the catheter for insertion of the catheter and the porous medium into the body, and (ii) a distal position in which a portion of the porous medium is located outside the catheter for treatment of the defect; wherein a cross-section of the shape of the porous medium includes one or more spokes extending radially outward, wherein two adjacent spokes are separated by a separation region, wherein the separation region is more flexible and/or compressible than the spokes.

18 Claims, 5 Drawing Sheets

(56) References Cited

U.S. PATENT DOCUMENTS

Figures 1A, 1B:
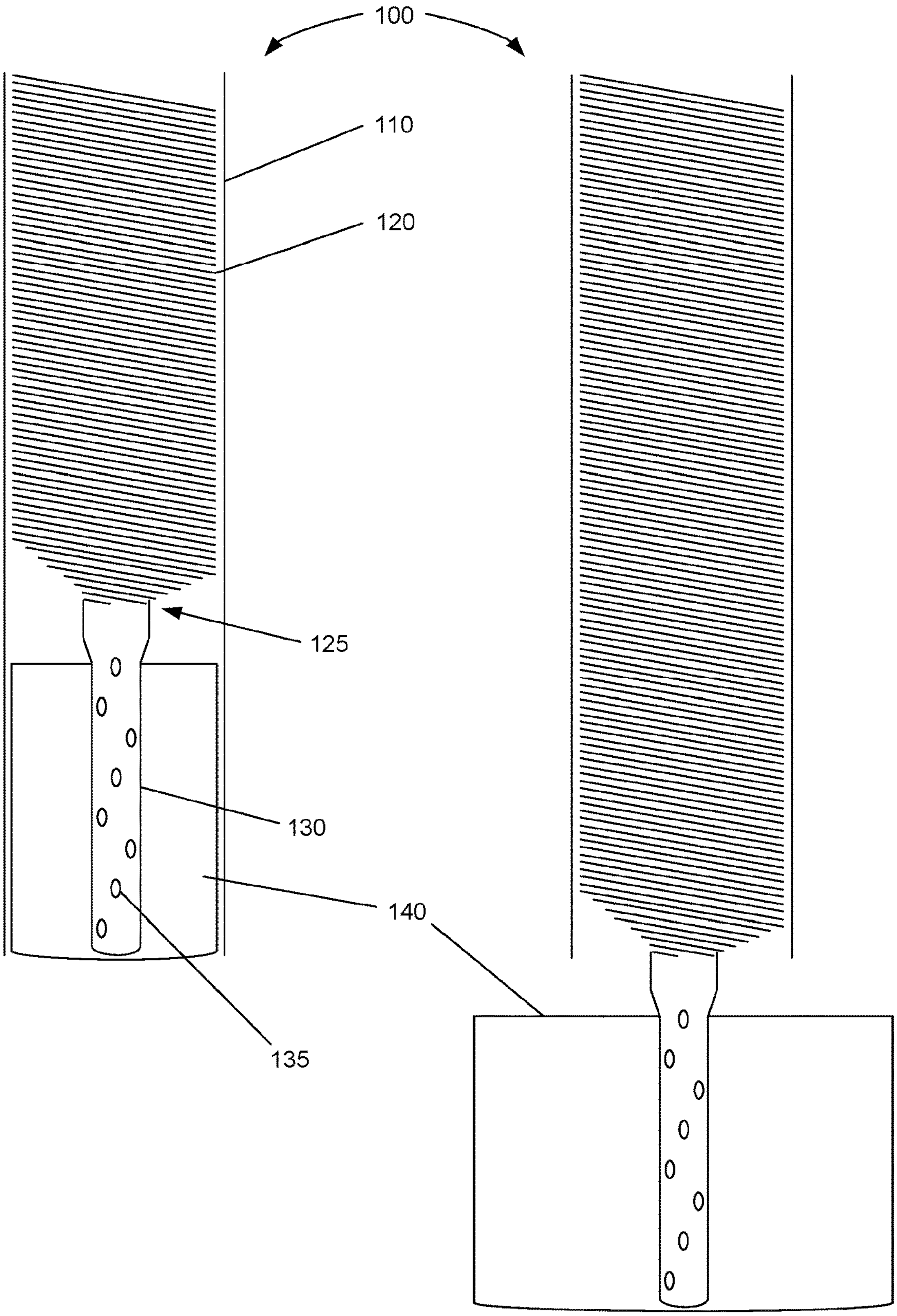

| | | | |
|---|---|---|---|
| 2020/0276056 | A1 | 9/2020 | Leeds |
| 2020/0360578 | A1 | 11/2020 | Loske et al. |

FOREIGN PATENT DOCUMENTS

| | | | |
|---|---|---|---|
| WO | WO 2010/080667 | A1 | 7/2010 |
| WO | WO 2013/084945 | A1 | 6/2013 |
| WO | WO 2017/182827 | A1 | 10/2017 |
| WO | WO 2018/200051 | A1 | 11/2018 |
| WO | WO 2022/157513 | A2 | 7/2022 |

OTHER PUBLICATIONS

WO2013084945 machine translation.
GB2100885.9 Combined Search and Examination Report.
PCT/GB2022/050183 International Search Report dated Aug. 12, 2022.
PCT/GB2022/050183 Written Opinion.

* cited by examiner

VACUUM THERAPY DEVICES AND METHODS

TECHNICAL FIELD

The present disclosure relates to devices and methods for treatment of defects internal of a human or animal body, such as abscesses and abscess cavities. The present disclosure provides apparatuses and methods for treating such internal defects through the application of a negative pressure at the site of the defect, e.g. to assist closure of an abscess cavity and/or to remove bodily fluids that may have accumulated at the defect.

BACKGROUND

Abscess cavities may include breaches in the continuity of the wall of the upper and lower gastrointestinal (GI) tract, which can create internal defects known as 'leak cavities'. Such breaches may be a result of anastomotic leak or spontaneous/iatrogenic perforation, which can often result in severe sepsis. Traditionally, open surgery and/or radiological drainage is required to treat such defects, though this approach is often associated with high rates of morbidity and mortality, and furthermore may not always be feasible. It is estimated that around 50% of patients who have a leak from the upper gastrointestinal (GI) tract that requires surgical intervention do not recover.

Abscesses occurring in the peritoneal and pleural cavities usually occur due to bacterial infection within that cavity, for example following visceral perforation in the peritoneal cavity, such as perforated appendicitis or perforated diverticulitis, or following pneumonia or other insult such as penetrating trauma in the pleural cavity. It is recognised that drainage of the cavity (i.e. removing contaminants) can help to control infection at these internal defects, though drainage by way of surgery is associated with increased morbidity and mortality.

It is desirable to provide an apparatus and method for treating such internal defects that may avoid the need for open surgery.

WO 2017/182827 A1 discloses devices and methods for treatment of internal defects of a human or animal body. It discloses a catheter including a tube, an applicator and a porous medium, wherein the applicator can be controlled at a proximal end of the tube to deploy the porous medium from a distal end of the tube to treat the defect.

SUMMARY

Aspects of the disclosure are set out in the independent claims and optional features are set out in the dependent claims. Aspects of the disclosure may be provided in conjunction with each other, and features of one aspect may be applied to other aspects.

In an aspect, there is provided a vacuum therapy device for treatment of a defect internal of a human or animal body. The device comprises: a porous medium for treatment of the defect, wherein a hollow passageway extends through at least a portion of the porous medium; a catheter having a proximal end and a distal end, wherein the catheter is configured to be inserted into the body to enable deployment of the porous medium through an opening at the distal end for treatment of the defect; and a suction element within the catheter, the suction element comprising a suction tube at least partially within the hollow passageway of the porous medium, wherein the suction tube has a plurality of fenestrations therein. The porous medium is movable between: (i) a proximal position in which a majority of the porous medium is inside the catheter for insertion of the catheter and the porous medium into the body, and (ii) a distal position in which a portion of the porous medium is located outside the catheter for treatment of the defect. The fenestrations of the suction tube are arranged to provide suction at a plurality of different locations along the porous medium.

Embodiments may enable a more uniform application of negative pressure at the porous medium. In turn this may provide a more uniform application of suction to the defect, and more uniform distribution of healing of tissue at the defect. Embodiments may enable the provision of a device with a suction tube which is both flexible enough to avoid inflicting trauma to the internal of a patient and also operable to provide a sufficient amount of suction at the porous medium. The plurality of fenestrations may enable suction to be provided to the porous medium even if other fenestrations have been blocked (e.g. by matter inside the body). Movement within the patient of the suction tube and the porous medium may be controlled by movement of an inner tube connected to the suction tube, thereby reducing the number of components needed to pass through the catheter to control operation of the device. The catheter may be utilised to place the porous medium into the defect, optionally under endoscopic visualisation or radiological guidance, depending on the defect.

The plurality of fenestrations may extend along the portion of the suction tube within the hollow passageway of the porous medium. For example, the majority of the fenestrations may be located within the hollow passageway, such as all the fenestrations. The hollow passageway may comprise a hollow core extending along a central axis of the porous medium (e.g. along a longitudinal axis of the porous medium, such as within the middle of the porous medium). The porous medium may be deformable to fit within the catheter. The porous medium may be configured so that at least a portion of the porous medium retains its pre-deformed shape when deployed from the catheter.

The fenestrations may have rounded corners. For example, the fenestrations may be polygonal with rounded corners, such as square shaped with rounded corners, or the fenestrations may be more rounded, such as ovaloid or circular in shape. Rounded corners of the fenestrations may reduce the likelihood of tearing of the suction tube. The fenestrations may be arranged in the suction tube in a stepped manner, so that adjacent fenestrations are both laterally and longitudinally offset from each other, e.g. the fenestrations may be arranged in different regions along the length of the suction tube, as well as in different regions around the circumference of the suction tube. The suction tube may have five or more fenestrations, such as ten or more, such as 15 or more. For example, each fenestration may have a greater area than the area of the hole at the end of the suction tube. The fenestrations may have a total open area of at least 5 $mm^2$, such as at least 10 $mm^2$, such as at least 15 $mm^2$, such as at least 20 $mm^2$, such as at least 25 $mm^2$, such as at least 30 $mm^2$, such as at least 35 $mm^2$, such as at least 40 $mm^2$. For example, each individual fenestration may have an open area of at least 0.5 $mm^2$, such as at least 0.75 $mm^2$, such as at least 1 $mm^2$, such as at least 1.25 $mm^2$, such as at least 1.5 $mm^2$, such as at least 1.75 $mm^2$, such as at least 2 $mm^2$. The region of the suction tube having the fenestrations may be less than 100 mm in length, such as less than 80 mm in length, such as less than 60 mm in length, such as less than 50 mm in length.

A cross-section of a shape of the porous medium may include one or more spokes extending radially outward. Each spoke may be tapered. For example, each spoke may decrease in width as it extends radially outwards, such as so that each spoke is narrower at its most radially outward point than at a more radially inward point. For example, the spoke may continuously taper from a central region of the porous medium to the tip. Each spoke may have a rounded tip. The cross-section of the shape of the porous medium may include at least two spokes extending radially outward. Two adjacent spokes may be separated by a separation region (e.g. a compression segment). The separation region may be more flexible and/or compressible than the spokes. The separation region may comprise at least one of: (i) less dense porous medium, and (ii) no porous medium. The separation region may be larger than a pore size of the porous medium. For example, the porous medium may be shaped to have an inner annular portion of porous medium arranged to define the hollow passageway through the porous medium. The porous medium may comprise one or more spokes of porous medium which extend radially outward from this inner annular portion of porous medium. The separation region may correspond to regions in which no, or less dense, porous medium extends radially outward from the inner annular portion of porous medium. The separation region may comprise the empty space, or space filled with less dense porous medium, between adjacent spokes in a region radially outward from the inner annular portion of porous medium.

The porous medium may include one or more compression segments (e.g. separation regions) comprising less dense and/or no porous medium. Compression segments are at least partially surrounded by porous medium, for example wherein the compression segments are encompassed within an outer perimeter of the porous medium. A transverse cross-section of the shape of the porous medium may be at least one of: (i) non-circular, or (ii) include one or more cutaway portions without porous medium. A shape of the porous medium may be selected to facilitate compression of the porous medium for insertion into the catheter, and/or to increase flexibility of the compressed porous medium within the catheter. The shape of the porous medium may be selected to have increased compression and/or flexibility as compared to a cylinder of comparable size (e.g. of a cylinder having the same diameter as the diameter of the spokes of the porous medium).

The cross-sectional shape of the porous medium may have a plurality of spokes. Spokes may comprise regions where the material of the porous medium extends radially outward with no material (or more flexible/less dense material) adjacent the radially extending region of porous medium. Spokes may enable greater compressibility and/or flexibility of the porous medium. The spokes may be tapered so that they are wider closer to the centre of the porous medium and narrower towards the radial tip of the spoke. Tapered spokes may facilitate removal from the defect after treatment, as they may reduce the likelihood of the porous medium tearing (rather than being pulled out from the tissue). For example, it may be more likely that the whole of the tip will come out if it is part of a tapered spoke. The spoke tapering may be continuous or it may occur in discrete chunks. The side profile of the spoke may have a straight edge, or it may be arcuate. There may be three spokes (or four or five or six or more). The spokes may have a rounded tip. Rounded tips may inhibit irritation or abrasion of the tissue internal of the patient (as compared to sharper tips).

Rounded tips may also be less likely to provide an impact trauma to internal regions of the patient during deployment.

The suction element may comprise an inner tube for connecting the suction tube to a source for providing negative pressure. The inner tube may run inside the catheter from its connection to the suction tube to a proximal end of the catheter. The inner tube may be provided at least in part by a coiled wire. The coiled wire may be arranged to stretch or bend in such a way that it does not provide a fluid tight seal. For example, negative pressure applied to the catheter or to the coil may be transferred within the catheter (e.g. so that negative pressure is present through both the coil and the catheter). The negative pressure may therefore be delivered to the porous medium both at its proximal end (from the catheter) and throughout the hollow passageway and at the distal end of the hollow passageway (from the inner tube and suction tube).

The device may be arranged to inhibit friction between the catheter and the inner tube (e.g. to permit movement of the inner tube, and thus the porous medium, relative to the catheter). For example, one or both of the inner tube and the catheter may comprise a coating configured to reduce friction therebetween. For example, the catheter may comprise an inner lining arranged to inhibit friction between the catheter and the inner tube. The inner lining may be made of a material arranged to reduce friction, such as fluorinated ethylene propylene. The inner lining may be adhered, or sewed, to the inside of the catheter, and/or it may just sit within the catheter without being affixed thereto. For example, the device may be arranged for flushing with a lubricant, e.g. to facilitate more friction reduction between the inner tube and the catheter. The lubricant may comprise an aqueous based fluid, such as saline. Coatings for the inner tube and/or catheter may comprise a friction lowering chemical. A distal region of the suction tube may be connected to a more proximal region of the device by a wire or suture. The suction tube may be stiffer than the porous medium. The Young's modulus of the suction tube may be greater than that of the porous medium.

The catheter may comprise an annular piece of tubing. A thickness of the annular piece of material which forms the annular tubing of the catheter may vary along the length of the catheter. For example, the material at the distal end of the catheter may be thinner than in other regions of the catheter to provide a greater internal diameter of the catheter at is distal end. For example, a majority of the length of the catheter may be formed of material of a selected thickness, while a distal end of the catheter is formed of material which is less thick than the selected thickness. The catheter may therefore have a larger internal diameter at its distal end, while retaining the same external diameter as in other regions of the catheter. The thinned material at the end of the catheter may enable a greater volume of porous medium to be stored in the catheter while still keeping the catheter of the same size. The catheter may be arranged so that the thinned region of the material is located only in the region where the porous medium will be stored during insertion of the device into the body. The thinner material region may be more flexible/weaker than other regions of the catheter, but this region may be supported physically by the porous medium (e.g. so that when the porous medium is loaded within the catheter, it supports this region of the catheter, and/or so that when the porous medium is deployed, the inner tubing extending from within the catheter to the porous medium provides support to said region).

The catheter may be arranged to define an internal ledge near the distal end of the catheter where the internal diameter of the catheter transitions from a larger diameter to a smaller diameter. The larger diameter may be on the distal side to the smaller diameter. The ledge may be arranged to hold the porous medium in place, e.g. to prevent the porous medium from travelling proximally up the catheter (further than the location of the ledge). For example, the internal diameter of the catheter may transition from the larger diameter to the smaller diameter in the region where the thickness of the catheter material changes from the thinner material (at the distal end) to the thicker material (on the proximal side). The ledge may be at a distance from the distal end of the catheter selected based on a length of the porous medium. For example, the ledge may be at a selected length from the distal end of the catheter, wherein the selected length is selected so that the porous medium will abut the ledge (e.g. will be held in place by the ledge/prevented from travelling further proximally up the catheter), with a volume of porous medium still extending out of the distal end of the catheter. This volume extending out of the distal end of the catheter may be small compared to a total volume of the porous medium (e.g. less than half the total volume). The volume of porous medium extending out of the distal end of the catheter may be for providing a soft leading edge of the catheter during insertion into the body (e.g. the material of the porous medium may be softer and more atraumatic than that of the catheter). The catheter may be arranged to receive the full porous medium with no porous medium protruding out of the distal end of the catheter, or the catheter may be arranged to receive only a portion of the porous medium so that a portion protrudes out of the distal end of the catheter.

The device may be an endoluminal vacuum therapy device configured for treatment of an abscess in the gastrointestinal tract. The device may be configured for insertion into the gastrointestinal tract through a nose or mouth of the human or animal body. The defect may be an abscess cavity, possibly caused by a breach in the wall of the lower or upper gastrointestinal (Cl) tract, including in the pharynx and oesophagus, whereby the catheter may be adapted for insertion into the body to access the defect endoluminally. The device may be a percutaneous vacuum therapy device configured for treatment of a defect in a peritoneal or pleural cavity of the human or animal body. The device may comprise one or more guidewires to facilitate insertion of the catheter to the desired location in the human or animal body. The defect may be an abscess in the peritoneal and pleural cavity, possibly caused by bacterial infection, whereby the catheter may be adapted for insertion into the body to access the defect percutaneously, and optionally using radiological guidance.

The apparatus may further be suitable for drainage, such as for drainage of an abscess cavity, whether in the abdominal or thoracic cavity, optionally wherein the catheter is arranged to be inserted percutaneously.

The device may comprise a pump (e.g. a vacuum apparatus) connected to the inner tube (whether directly or indirectly) and/or the catheter (e.g. at a proximal end thereof). The device may be configured so that the inner tube may be connected with the pump and the porous medium to provide suction (e.g. negative pressure) at the porous medium. The device may comprise a receptacle connected to the inner tube and/or catheter. For example, the receptacle may connect to the catheter to allow collection of fluid from both the inner tube and the catheter. The receptacle may be configured to receive substances sucked up through the suction tube. The inner tube and/or catheter may be arranged for connection to one or more fluid delivery devices. For example, the inner tube and/or catheter may be arranged to be connected to a syringe for providing fluids to the device, such as a lubricant for facilitating relative movement between the inner tube and the catheter or a fluid for flushing tissue from the porous medium (e.g. saline). Suction tubes of the present disclosure may be formed from silicon, or a suitable polymer such as PVC (polyvinyl chloride).

In an aspect, there is provided a vacuum therapy device for treatment of a defect internal of a human or animal body. The device comprises: a porous medium for treatment of the defect; a catheter having a proximal end and a distal end, wherein the catheter is configured to be inserted into the body to enable deployment of the porous medium through an opening at the distal end for treatment of the defect; and a suction element within the catheter, the suction element comprising a suction tube connected to the porous medium to provide suction thereat. The porous medium is movable between: (i) a first position inside the catheter for insertion of the catheter and the porous medium into the body, and (ii) a second position in which a portion of the porous medium is located outside the catheter for treatment of the defect. A cross-section of the shape of the porous medium includes one or more spokes extending radially outward, wherein two adjacent spokes are separated by a separation region, wherein the separation region is more flexible and/or compressible than the spokes.

A hollow passageway may extend through a portion of the porous medium. The suction tube may be at least partially within the hollow passageway. The suction tube may have a plurality of fenestrations therein. The fenestrations may extend along the portion of the suction tube within the hollow passageway of the porous medium. For this aspect, the porous medium, the suction tube and/or other features of the device may correspond to those described in the first aspect described above.

In an aspect, there is provided a porous medium configured to be used in a vacuum therapy device for treatment of a defect internal of a human or animal body. The device comprises: (i) a catheter having a proximal end and a distal end, wherein the catheter is configured to be inserted into the body to enable deployment of the porous medium through an opening at the distal end for treatment of the defect; and (ii) a suction tube within the catheter. A hollow passageway extends through the porous medium, the hollow passageway being configured to receive a said suction tube therein to provide suction. A cross-section of the shape of the porous medium includes a plurality of spokes extending radially outward, wherein two adjacent spokes are separated by a separation region, wherein the separation region is more flexible and/or compressible than the spokes. For this aspect, the porous medium may correspond to that described in the first and second aspect described above.

In an aspect, there is provided a vacuum therapy device for treatment of a defect internal of a human or animal body. The device comprises: a porous medium for treatment of the defect, wherein a hollow passageway extends through at least a portion of the porous medium; a catheter having a proximal end and a distal end, wherein the catheter is configured to be inserted into the body to enable deployment of the porous medium through an opening at the distal end for treatment of the defect; and a suction element within the catheter, the suction element comprising a suction component at least partially within the hollow passageway of the porous medium. The porous medium is movable between: (i) a proximal position in which a majority of the porous medium is inside the catheter for insertion of the catheter and the porous medium into the body, and (ii) a distal position in which a portion of the porous medium is located outside the catheter for treatment of the defect. The suction component comprises one or more open channels extending along a majority of the length of the porous medium to provide suction at along the length of the porous medium.

For example, the suction component may be cruciate shaped in cross section. The cruciate shape may define a plurality of channels extending along a length of the component. For example, the cruciate shape may comprise a plurality of flanges extending radially outward, such as extending radially outward from a central region of the suction component. Each of the radially extending flanges may also comprise a lip at their radially outer end, wherein the lip extends circumferentially from the radially outer end of the flange. The spacing between adjacent flanges and their respective lips may define the channels. For example, because each flange and its respective lip(s) do not touch adjacent flanges/lips, the suction component will define channels which are only partially sealed, e.g. so that suction applied to the suction component at its proximal end (e.g. by the inner tube) may be transferred to each channel at the proximal end. Due to the channels not being sealed at each radial point along their length, suction will be transferred out through the channels to porous medium adjacent the channels. The suction component is shaped so that the suction is delivered along its length (to surrounding porous medium). For example, the suction component may be shaped like a cross potent (e.g. crutch cross) when viewed in cross section. The cross bars at the four ends of the cross may be curved (as if sections of a circumference of a circle connecting the four ends). The four ends may extend toward each other, but not so far as to touch each other. A different shape to a cross may be used, for example so that there are a different number of flanges/cross bars (e.g. at the ends of the flanges). For example, the shape may be arranged with 2 cross bars provided, or 3 cross bars may be provided, or five or more.

In an aspect, there is provided a vacuum therapy device for treatment of a defect internal of a human or animal body. The device comprises: a porous medium for treatment of the defect, wherein a hollow passageway extends through at least a portion of the porous medium; a catheter having a proximal end and a distal end, wherein the catheter is configured to be inserted into the body to enable deployment of the porous medium through an opening at the distal end for treatment of the defect; and a suction element within the catheter, the suction element comprising a suction tube at least partially within the hollow passageway of the porous medium and an inner tube coupled to the suction tube and extending to the proximal end of the catheter. The porous medium is movable between: (i) a proximal position in which a majority of the porous medium is inside the catheter for insertion of the catheter and the porous medium into the body, and (ii) a distal position in which a portion of the porous medium is located outside the catheter for treatment of the defect. An inner surface of the catheter comprises a layer of friction reducing material, such as fluorinated ethylene propylene, to reduce friction between the inner tube and the catheter.

In an aspect, there is provided a vacuum therapy device for treatment of a defect internal of a human or animal body. The device comprising: a porous medium for treatment of the defect, wherein a hollow passageway extends through at least a portion of the porous medium; a catheter having a proximal end and a distal end, wherein the catheter is configured to be inserted into the body to enable deployment of the porous medium through an opening at the distal end for treatment of the defect; and a suction element within the catheter, the suction element comprising a suction tube at least partially within the hollow passageway of the porous medium. The porous medium is movable between: (i) a proximal position in which a majority of the porous medium is inside the catheter for insertion of the catheter and the porous medium into the body, and (ii) a distal position in which a portion of the porous medium is located outside the catheter for treatment of the defect. The material at the distal end of the catheter is thinner than in other regions of the catheter to provide a greater internal diameter of the catheter at its distal end. The material of the catheter transitions from being thinner to thicker to define an internal ledge near the distal end, wherein the internal ledge is arranged to inhibit further proximal movement of the porous medium within the catheter.

The ledge may be arranged at a location so that a portion (e.g. a small portion) of the porous medium protrudes out the distal end of the catheter when the porous medium abuts the inner ledge. In other examples, the inner ledge may be arranged to enable porous medium to be inserted all the way into the catheter.

Aspects of the present disclosure may be provided in combination with a deployment applicator for controlling deployment of the porous medium (e.g. for providing distal movement of the porous medium relative to the catheter). Such a deployment applicator may be actuatable by a user (e.g. one-handed) to provide controlled deployment. This may include actuating the applicator by moving one (moving) portion of the applicator relative to another (stationary) portion. This relative movement of the deployment applicator may be translated into a corresponding movement of the porous medium relative to the catheter.

In an aspect, there is provided a vacuum therapy system comprising: any of the vacuum therapy devices disclosed herein; and a deployment applicator arranged to couple to the catheter and the suction element of the vacuum therapy device, and wherein the deployment applicator is actuatable to control deployment of the porous medium from its proximal position to its distal position.

The deployment applicator may comprise: a catheter coupling arranged to hold the catheter of the vacuum therapy device in a fixed position; and a movable element arranged to couple to the suction tube of the vacuum therapy device for controlling movement thereof. The movable element may be movable relative to the catheter coupling to provide a corresponding movement of the suction tube relative to the catheter (e.g. and thus to also provide relative movement of the porous medium relative to the catheter). The movable element may be movable between: (i) a retraction position in which the porous medium is located in its proximal position, and (ii) a deployment position in which the porous medium is located in its distal position. Movement between the retraction position and the deployment position may comprise one or both of: (i) movement from the retraction position towards the deployment position, and (ii) movement from the deployment position towards the retraction position.

For example, the movable element may be arranged to couple to the suction tube so that movement of the movable element in a first direction provides a corresponding distal movement of the suction tube and porous medium relative to the catheter. Additionally, the movable element may be arranged to couple to the suction tube so that movement of the movable element in a second direction provides a corresponding proximal movement of the suction tube and porous medium relative to the catheter. In other words, the movable element may be arranged to couple to the suction tube and catheter to enable the applicator to control deployment of the porous medium, and optionally to also enable the applicator to control retraction of the porous medium. The movable element may be arranged to engage with the suction tube to provide such bidirectional movement (e.g. retraction and deployment). For example, the movable element may be arranged to grip, clip to, and/or slot into the suction tube. This may enable bidirectional movement of the porous medium into and out of the distal end of the catheter when the movable portion of the deployment applicator is moved (e.g. proximally and distally) relative to the stationary portion of the deployment applicator.

The applicator may comprise a moving portion and a stationary portion. Each portion may have at least one gripping region for holding by a user of the deployment applicator. The applicator may be configured for one-handed use. The at least one gripping region of one of the moving portion and the stationary portion may comprise a thumb loop arranged to receive a user's thumb. The at least one gripping region of the other of the moving portion and the stationary portion may comprise a finger loop arranged to receive a user's finger. The portion of the applicator which comprises the finger loop may further comprise one or more additional finger loops. For example, that portion of the applicator may have two finger loops. Each of the finger loops may be arranged to receive a respective finger, so that the user may control the applicator using their thumb and two or more of their fingers. For example, the applicator may be arranged to be controlled by the user using their thumb (in the thumb loop) and two of their fingers (each in a respective finger loop). The stationary portion may have the (one or more) finger loop(s) and the moving portion may have the thumb loop. The stationary portion may have two finger loops for receiving a user's index and middle fingers. The stationary portion of the applicator may be provided by a proximal portion of the catheter. The gripping region may comprise one or more ridges or protrusions, optionally for increasing a user's grip in that region.

The applicator may be arranged such that relative movement of the user's thumb in the thumb loop relative to their finger(s) in the finger loop(s) provides the corresponding movement of the porous medium relative to the catheter. The applicator may comprise a movement indicator mechanism arranged to provide feedback about deployment and/or retraction of the porous medium by the applicator. The movement indicator mechanism may be arranged to provide at least one of audible, tactile and/or visible feedback about movement of the porous medium relative to the catheter by the deployment applicator. The moving portion may be arranged to interact with the stationary portion to provide the movement indicator mechanism. A body of the moving portion may be slidably received in a receiving channel of the stationary portion, and wherein sliding of the body through the receiving channel may be arranged to provide the feedback. At least one of the body and the receiving channel may have a textured surface arranged to provide vibrations in response to sliding of the body through the receiving channel for providing audible and/or tactile feedback. The applicator may comprise one or more measurement indicia arranged to provide an indication of a distance of movement of the movable element relative to the catheter coupling. The applicator may be configured for deployment and/or retraction of the porous medium relative to the catheter. The applicator may be arranged to be detachable from the catheter (e.g. for removing the applicator from the catheter after the porous medium has been deployed).

In an aspect, there is provided a deployment applicator configured to be used with a vacuum therapy device for treatment of a defect internal of a human or animal body, the vacuum therapy device comprising: a porous medium for treatment of the defect; a catheter having a proximal end and a distal end, wherein the catheter is configured to be inserted into the body to enable deployment of the porous medium through an opening at the distal end for treatment of the defect; and a suction element within the catheter, the suction element comprising a suction tube connected to the porous medium to provide suction thereat, wherein the deployment applicator comprises: a catheter coupling arranged to hold the catheter of a said vacuum therapy device in a fixed position; and a movable element arranged to couple to the suction tube of said vacuum therapy device for controlling movement thereof. The deployment applicator is actuatable to control movement of the movable element relative to the catheter coupling to provide a corresponding movement of the porous medium of said vacuum therapy device between: (i) a proximal position in which a majority of the porous medium is inside the catheter for insertion of the catheter and the porous medium into the body, and (ii) a distal position in which a portion of the porous medium is located outside the catheter for treatment of the defect.

Aspects of the present disclosure may comprise a kit of parts for a vacuum therapy system, the kit comprising: any of the vacuum therapy devices disclosed herein, and any of the deployment applicators disclosed herein.

In an aspect, there is provided a method of treatment of a defect internal of a human or animal body. The method comprises: inserting an vacuum therapy device into the body, wherein the device comprises: (i) a catheter having a proximal end and a distal end, and (ii) a porous medium for insertion into the defect, wherein a majority of the porous medium is located within the catheter during insertion into the body; positioning the catheter in the body to enable deployment of the porous medium into the defect; deploying at least a portion of the porous medium through an opening at the distal end of the catheter for treatment of the defect; applying suction at a plurality of locations of the porous medium inserted in the defect.

The method may be a method of treatment of a defect in the gastrointestinal tract of the human or animal body. The method may comprise insertion of the catheter through the nose or mouth of the human or animal.

The method may be a method of treatment of a defect in a peritoneal or pleural cavity of the human or animal body. The method may comprise percutaneous insertion of the catheter into the human or animal body.

Aspects of the present disclosure may provide methods of manufacture of devices disclosed herein. In such aspects, porous medium may be obtained. The porous medium may be obtained in a cylindrical form. The cylindrical form of the porous medium may be cut back so that a volume of porous medium is removed therefrom without shrinking the effective maximum diameter of the porous medium (e.g. the spokes of the porous medium may have the same diameter of the circle from which the material is being cut).

FIGURES

Some examples of the present disclosure will now be described, by way of example only, with reference to the figures, in which:

FIGS. 1*a* and 1*b* show a schematic diagram of an exemplary vacuum therapy device.

Figure 2A:
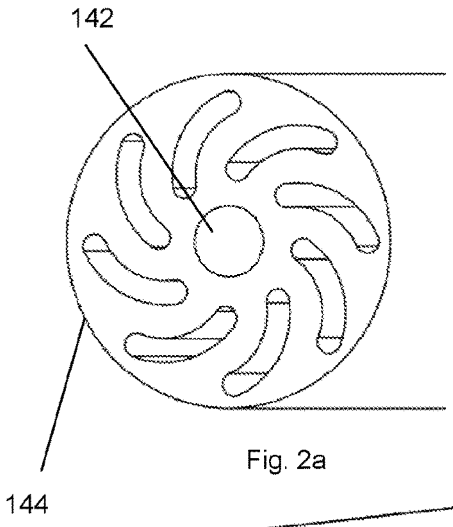
Figure 2B:
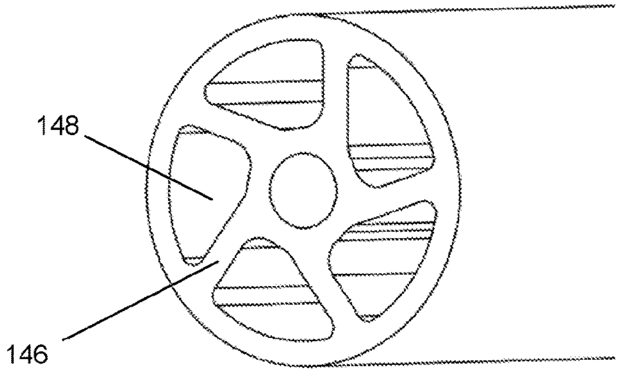
Figure 2C:
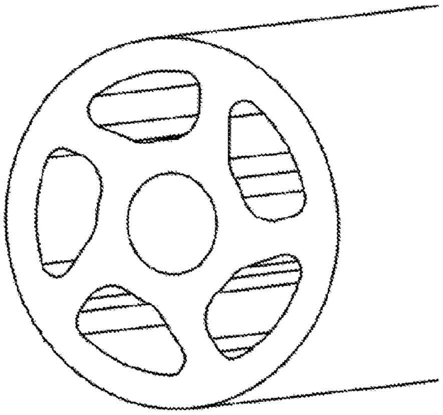
Figure 2D:
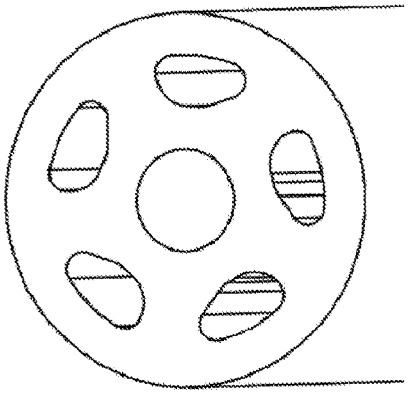
Figure 2E:
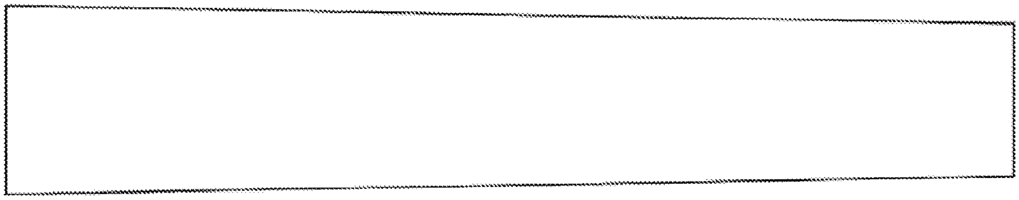
Figure 2F:
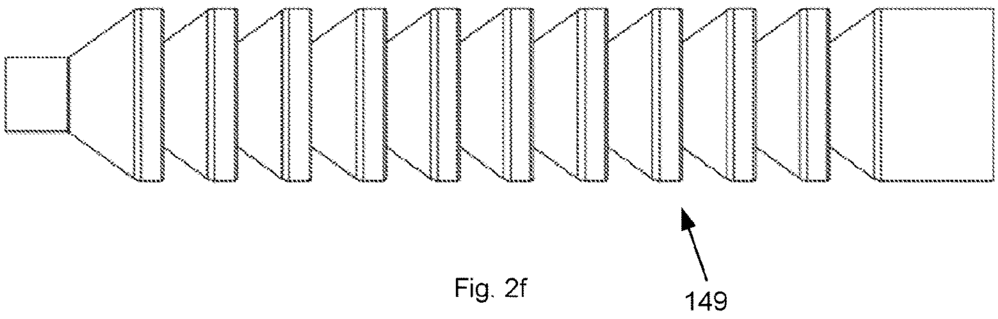
Figure 2G:
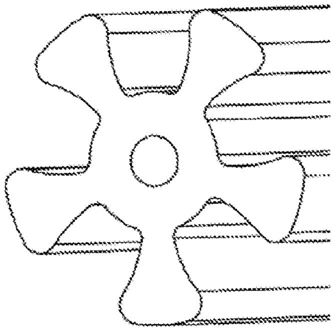
Figure 2H:
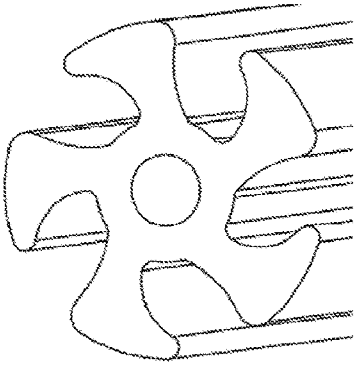
Figure 2I:
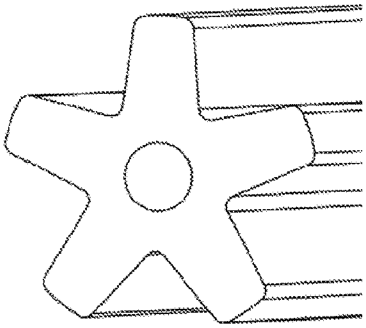
Figure 2J:
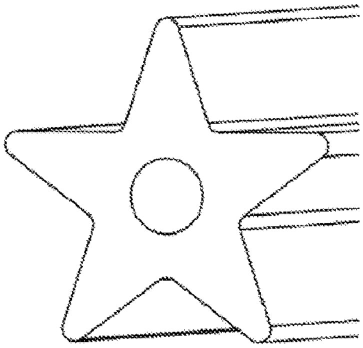
Figure 2K:
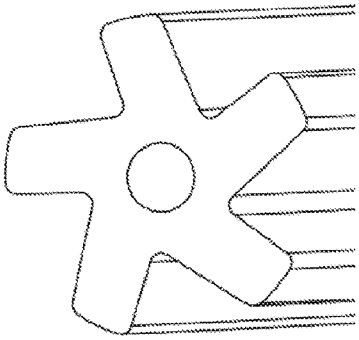
Figure 2L:
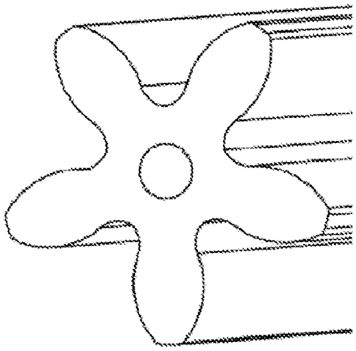
Figure 2M:
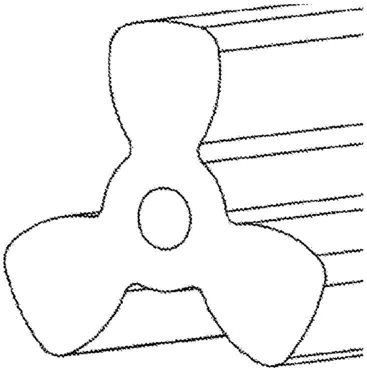
Figure 2N:
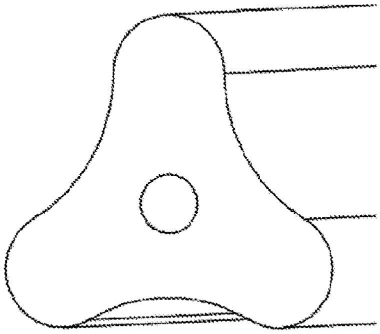
Figure 2O:
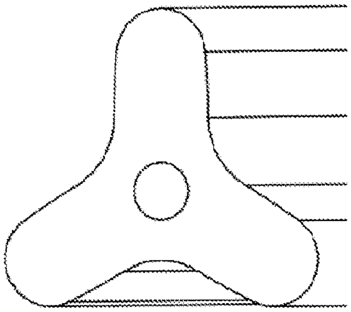
Figure 2P:
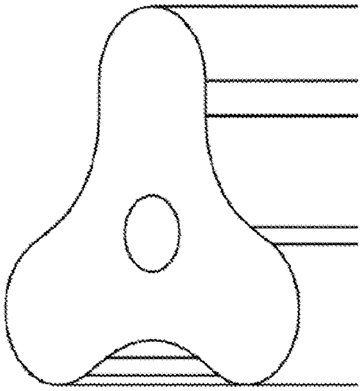
Figure 2Q:
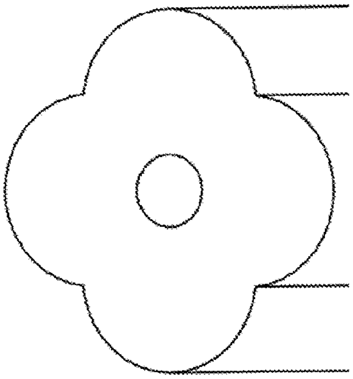
Figure 2R:
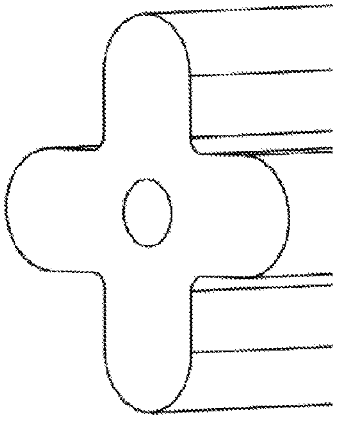

FIGS. 2*a* to 2*r* show example shapes for the porous medium of the device of FIGS. 1*a* and 1*b*.

FIGS. 3*a* to 3*d* show a deployment applicator, such as for controlling deployment of the porous medium for the vacuum therapy device shown in FIGS. 1*a* and 1*b*.

In the drawings like reference numerals are used to indicate like elements.

SPECIFIC DESCRIPTION

Embodiments of the present disclosure are directed to vacuum therapy devices for treatment of a defect internal of a human or animal body. Embodiments include a porous medium for treatment of the defect by placement of the porous medium in the defect, and by application of a negative pressure to the porous medium when located in the defect. The porous medium may be connected to a suction tube which is arranged to provide this negative pressure (e.g. suction) at different points along a length of the porous medium. This may provide a more even distribution of negative pressure at the porous medium, and so the defect may heal more uniformly (e.g. tissue may interact with a greater surface area of the porous medium). This may also enable negative pressure to be provided to the porous medium even if fenestrations in the suction tube for providing negative pressure have been obstructed or blocked by substances inside the body. The porous medium may be shaped to facilitate insertion into the human or animal of a catheter which houses the porous medium. That is, the porous medium may be shaped for compressibility and flexibility to improve the ability of the porous medium (and catheter housing it) to curve round bends when they are being passed through body lumens to their intended location in the body.

FIGS. 1*a* and 1*b* show a vacuum therapy device 100. The vacuum therapy device 100 includes a catheter 110, a suction element comprising an inner tube 120 and a suction tube 130, and a porous medium 140. In FIG. 1*a*, the device 100 is in an insertion position with the porous medium 140 inside the catheter 110. In FIG. 1*b*, the device 100 is in a deployed position with the porous medium 140 outside the catheter 110.

The inner tube 120 is located within the catheter 110. The inner tube 120 is connected to the suction tube 130 at connection 125. The suction tube 130 is located distally of the inner tube 120. The suction tube 130 is connected to the porous medium 140 by being arranged within a hollow passageway of the porous medium 140. For example, the suction tube 130 may be adhered to (e.g. bonded and/or glued to) the porous medium 140, such as within the hollow passageway of the porous medium 140. The suction tube 130 extends through the porous medium 140 to a distal end of the porous medium 140.

The vacuum therapy device 100 in this example is an endoscopic vacuum therapy (EVT) device. Endoscopic vacuum therapy is a relatively new technique for treating defects, such as oesophageal perforation and certain other leakages from the UGI tract, such as post-operative leakages. EVT is a minimally invasive, alternative method of treatment to traditional surgery, utilising vacuum-assisted closure (VAC) techniques. EVT involves placing a porous medium, such as a polyurethane sponge, into a defect cavity under endoscopic visualization and then applying a continuous negative pressure, causing the cavity to collapse around the sponge. The sponge is typically changed every 48-72 hours until the cavity shrinks and stable granulation tissue forms a barrier.

EVT includes three different stages for treating a gastrointestinal defect. For example, EVT may be used to treat a defect in the oesophagus. To treat the defect, a tube may be inserted through the nose or mouth and then directed to the defect under direct endoscopic visualisation. A porous medium may be carried into the patient in the tube and then placed in the defect cavity, or a lumen proximal thereto, such as a lumen of the bowel (e.g. for intra-luminal vacuum therapy). A negative pressure, such as −125 mm Hg, may then be applied, causing the defect cavity to collapse around the porous medium to aid healing. This treatment may also be referred to as endoscopic 'transluminal' or 'intraluminal' vacuum therapy.

The catheter 110 is elongate and tubular. The catheter 110 has a proximal end and a distal end. The distal end is the end which is to be inserted into the body and located at, or proximal to, the defect. The proximal end is the end which will be located towards the physician. To deliver the catheter 110 to a target location within the body, the catheter 110 may be inserted into an endoscope, or the catheter 110 may be attached to an endoscope external to the endoscope. The catheter 110 is of sufficient length to extend from outside the body to a location proximal to (or inside) the defect in the body. For example, the tube may have a length of between 0.5 m and 1.5 m depending on the patient and the location of the defect in the patient. A distal end of the catheter 110 may be flared open (e.g. tapered to a larger diameter). Alternatively, or additionally, the distal end of the catheter 110 may be made of thinner material so that the inner diameter of the catheter is larger in that region. The inner diameter being larger may enable a greater volume of porous medium 140 to be stored in the catheter 110. The region where the thickness of material of the catheter 110 increases may define a ledge which prevents the porous medium 140 moving proximally up the catheter 110. The ledge may also hold the porous medium 140 in place during insertion into the body. The porous medium 140 may be held in place so that a portion of the porous medium 140 extends out of the distal end of the catheter 110 to provide a soft leading edge during insertion into the body.

For examples where the catheter 110 may be inserted into an endoscope, the catheter 110 may have an outer diameter sized to fit within an endoscope, such as to fit within a working channel of an endoscope. The outer diameter may be sized to enable the catheter 110 to move relative to the endoscope when inside the endoscope. For example, the outer diameter may be less than 2.8 mm or 3.7 mm, depending on the endoscope with which the catheter 110 is to be used.

For examples where the catheter 110 may be attached to the endoscope external to the endoscope (e.g. the two may be adjacent to one another and affixed together), the catheter 110 may be provided with one or more attachment means (e.g. sutures) for affixing the catheter 110 to the endoscope. The catheter 110 may have a suture at the distal end, and an endoscopic grasper (or biopsy forceps) may be passed through the working channel of the endoscope, and used to grasp the suture. The forceps may then be pulled back into the working channel of the endoscope so the endoscope and catheter 110 lay side by side. The endoscope and catheter 110 may be advanced through the UGI tract to the leak site together, with the catheter 110 being pulled alongside the endoscope.

The inner tube 120 is elongate and tubular. An outer diameter of the inner tube 120 is sized to enable the inner tube 120 to fit within the catheter 110 (and to move relative thereto). The distal end of the inner tube 120 is located within the catheter 110 proximal to the distal end of the catheter 110. The distal end of the inner tube 120 is connected to a proximal end of the suction tube 130 at the connection 125. The inner tube 120 is of sufficient length to extend from outside the body to a location proximal to the defect. The inner tube 120 is provided by a coiled wire. The helical structure of the coiled wire extends along a longitudinal axis of the inner tube 120 thereby providing the hollow cross-section defining the tubular structure. A hollow cross-section may extend along the entire length of the components inside the catheter 110, for example, this may enable a wire to pass through the device to enable the device to be railroaded into a desired location in the body.

The suction tube 130 is elongate and tubular. The suction tube 130 is of sufficient length to extend into a hollow passageway of the porous medium 140 to connect the suction tube 130 to the porous medium 140. The suction tube 130 extends along a majority of the length of the porous medium 140. A distal tip of the suction tube 130 is located proximal to a distal end of the porous medium 140. The suction tube 130 is adhered to the porous medium 140 at a plurality of positions along its length. The suction tube 130 may be tapered so that the distal end of the suction tube 130 is at a smaller diameter, e.g. the suction tube 130 may have a larger diameter in a middle region along the length of the suction tube 130 than that at the distal end of the suction tube 130.

The suction tube 130 includes a plurality of fenestrations 135 (e.g. holes which provide a fluid flow path from the porous medium 140 into the hollow core of the suction tube 130). The fenestrations 135 are arranged along the length of the suction tube 130 which is inserted into the porous medium 140. The fenestrations 135 are distributed uniformly along the length of the suction tube 130, e.g. so that the number of fenestrations 135 per unit length remains constant along the length of the suction tube 130 within the porous medium 140. The fenestrations 135 are distributed both radially and axially along the suction tube 130. For examples where the suction tube 130 has a tapered structure at its proximal end (where it tapers from a wider diameter to a narrower diameter), the fenestrations 135 may only be in the narrowed portion of the suction tube 130 (on the side of the tapering with the smaller diameter). In other examples, where there is no tapering of the suction tube 130, the fenestrations 135 may be located on any part of the suction tube 130, e.g. they may only be located in the region of the suction tube 130 which is inserted into the porous medium 140.

The connection 125 between the suction tube 130 and the inner tube 120 comprises a screw thread type connection. The inside surface of the suction tube 130 at its proximal end includes a female screw thread. The coiled wire at the distal end of the inner tube 120 effectively provides a male screw thread. The coiled wire is screwed into the suction tube 130. Adhesive may also be used in this region for the attachment. The connection 125 between the suction tube 130 and the inner tube 120 is in the region of the suction tube 130 with the larger diameter.

The porous medium 140 has a hollow passageway in which the suction tube 130 is provided and connected thereto. The porous medium 140 is sized so that it is compressible to fit within the catheter 110. The porous medium 140 comprises a material having pores which are typically of a size between 400 to 600 microns. The porous medium 140 may include one or more materials such as: (i) foams e.g. a polyurethane foam, (ii) expandable meshes e.g. a wire mesh, (iii) bio-active materials e.g. bio-active collagen. For example, the wire mesh may be formed of a shape memory material, such as a nickel titanium alloy (e.g. nitinol).

The vacuum therapy device 100 is configured for insertion into a patient to be delivered to, or proximal to, a defect internal of the patient's body. In this example, the vacuum therapy device 100 is an endoscopic vacuum therapy device. The device 100 is arranged (e.g. sized and shaped) to be carried into the patient's body using an endoscope. For example, the device 100 may be arranged to be insertable into an endoscope, and/or the device 100 may be arranged so that it may be affixed to an endoscope (e.g. via suture so that the two are adjacent). The device 100 is configured so that when inserted into the patient with an endoscope, the endoscope and device 100 (e.g. the endoscope housing the device 100, or the endoscope adjacent the device 100) may pass through bends in the internal lumens of the patient. For example, the device 100 may be configured for treatment of defects in a patient's gastrointestinal tract. For this, the device 100 is configured to be inserted into a patient's nose (or their mouth, such as when the patient is already being ventilated). The device 100 is sufficiently flexible to pass round the bends on the way from the patient's nose or mouth into the defect their gastrointestinal tract.

The device 100 is arranged to be resistant to kinking during insertion into the patient's gastrointestinal tract. The device 100 may be configured to be sufficiently flexible to enable application of a mask (e.g. for oxygenation) to be provided to a patient receiving treatment. For example, the device 100 may be arranged to bend away from a patient's nose to avoid impeding a mask on the patient. The device 100 may be arranged to facilitate movement of the device 100 within a said endoscope (e.g. an outer surface of the device 100 may be configured to reduce friction with an endoscope, such as by having a friction-reducing coating). The device 100 may be arranged so that the endoscope and device 100 are separable when inside the patient (e.g. in response to force being applied to one of the endoscope or device 100, such as to tear the suture and/or by opening endoscopic graspers to release the suture). For example, the device 100 may be configured so that it is capable of twisting or bending with a radius of curvature of approximately 10 mm, such as 20 mm or less. For example, the device 100 may be configured to bend round 90 degrees or more without rupturing or kinking.

The catheter 110 is configured to be inserted into a patient. The catheter 110 is of sufficient flexibility to pass round bends in body lumens of a patient. The catheter 110 is arranged to avoid kinking during insertion into the patient. An inner surface of the catheter 110 may be configured to reduce friction between that inner surface and components inside the catheter 110 (e.g. the inner tube 120, suction tube 130 and/or porous medium 140). For example, the catheter 110 may have a friction reducing coating on its interior surface. In some examples, the catheter 110 may have a friction reducing layer on its inner surface. For example, a layer of fluorinated ethylene propylene may be provided on an inner surface of the catheter 110, e.g. this layer may be adhered to the inner surface of the catheter 110. A distal end of the catheter 110 may be configured to facilitate insertion (e.g. retraction) of a porous medium 140 into the catheter 110. For example, the distal end may be flared open, and/or may be formed of a thinner material.

The inner tube 120 is configured to be inserted to the catheter 110 and into a patient. The inner tube 120 is configured to be of sufficient flexibility to pass round bends in body lumens of a patient. The inner tube 120 is configured so that negative pressure applied to a proximal end of the inner tube 120 and/or the catheter 110 is transmitted to a distal end of the inner tube 120/catheter 110 and into the suction tube 130/porous medium 140. For example, where the inner tube 120 is provided by a wire coil, the wire coil may stretch during insertion/bending to follow the path to the intended location (e.g. adjacent turns of the coil may separate, and this may reduce a fluid seal provided by the inner tube 120). Negative pressure applied to the proximal region of the inner tube 120 or the catheter 110 may then be provided to the distal region of the inner tube 120, as well as to the porous medium 140 at the distal region of the catheter 110. In some examples, regions of the coil wire (such as those between adjacent turns of the coil) may be coated with a material configured to inhibit stretching therebetween, or the coil wire may be selected to be sufficiently stiff to longitudinal stretching (e.g. it may be selected to have a sufficiently high spring constant) so that motion of the inner tube 120 at its proximal end may provide movement of the porous medium 140 at its distal end.

The inner tube 120 is configured to move relative to the catheter 110. The inner tube 120 is configured to pass round bends—for example, the coil wire may provide increased flexibility as compared to a continuous tube of material. The inner tube 120 may be configured to reduce friction between the inner tube 120 and the catheter 110. For example, the outer surface of the inner tube 120 may have a coating for reducing friction between it and the inner surface of the catheter 110. Alternatively and/or additionally, the inner surface of the catheter 110 may have a coating for reducing friction between it and the inner tube 120 and/or the catheter 110 may have a material lining on its inner surface which reduces friction. The inner tube 120 may be formed of a biocompatible material and/or may be coated by a biocompatible substance.

Although not shown in the figures, the inner tube 120 and/or the catheter 110 may be connected to a source of negative pressure at its proximal end, e.g. both may be connected to the same source of negative pressure, e.g. both may be connected to the same connection. This connection to the source of negative pressure may be direct or indirect (via one or more additional components for transmitting negative pressure). For example, one connector may be provided for connection both the inner tube 120 and the catheter 110 to the same vacuum source. This connection may be arranged to slide over a proximal end of the inner tube 120 (e.g. where there may be a solid region, such as a rod). The connection may then couple to the catheter 110 once slid over this solid region. The device 100 is configured to transmit such negative pressure, so that it may be applied at the porous medium 140 to provide suction thereat. For example, a proximal end of the inner tube 120 may be secured to an adaptor for connection to a source of negative pressure, such as a vacuum apparatus. The device 100 may be arranged so that when in use, such an adaptor is located outside of the patient's body. The adaptor may provide a connector for coupling the inner tube 120 with the vacuum apparatus. The adaptor may be provided with a further connector, which is substantially in-line with the other connector, for coupling with a flexible tube (e.g. formed from FEP). The further connector may be provided with barbs, which a flexible tube may be stretched over so as to provide a secure fluid-tight coupling. Any suitable type of connector may be used, such as a lock connector, e.g. a luer lock connector.

The connection 125 between the suction tube 130 and the inner tube 120 is configured so that some negative pressure may be provided from the inner tube 120 to the suction tube 130 to enable suction to be provided at the porous medium 140 (and e.g. at a distal end of the suction tube 130). The device 100 is arranged so that air or other substances drawn into the suction tube 130 through the porous medium 140 pass up through the suction tube 130 into the inner tube 120 and out the proximal end of the inner tube 120 or the proximal end of the catheter 110. The inner tube 120 is connected to the suction tube 130 (and the suction tube 130 connected to the porous medium 140) so that movement of the suction tube 130 and porous medium 140 can be controlled by movement of the inner tube 120. The device 100 is arranged to enable a physician to interact with the inner tube 120 (or a component coupled with the inner tube 120) at a proximal location, e.g. outside the patient's body, to control movement of the suction tube 130 and porous medium 140 at a distal location, e.g. in or near to the defect internal of the patient.

The suction tube 130 is configured to provide suction at the porous medium 140. The suction tube 130 is configured to receive air or other substances which are transmitted into the suction tube 130 through the porous medium 140 and to transmit these away through the inner tube 120. The suction tube 130 is configured to be flexible with an atraumatic tip (e.g. to inhibit the suction tube 130 from causing damage to a patient when being moved around inside the patient). An outer surface of the suction tube 130 may be coated with an adhesive to facilitate a stronger connection between the suction tube 130 and the porous medium 140. A tip of the suction tube 130 may be coupled (e.g. via a wire or suture) to a component at a proximal location in the device 100 (such as the inner tube 120) to improve control of the movement of the suction tube 130, such as to facilitate removal of the suction tube 130 and porous medium 140 from a defect.

The fenestrations 135 are configured to provide fluid inlets to the suction tube 130. Fenestrations 135 are arranged at a plurality of locations along the suction tube 130 to enable air or other substances to pass into the suction tube 130 through the porous medium 140 at a plurality of locations. The fenestrations 135 enable suction to be provided at a plurality of different locations of the suction tube 130, and also to enable suction still to be provided in the event that one or more of the fenestrations 135 (or a hole at the end of the suction tube 130—if there is one) becomes obstructed or blocked by a substance inside the body. The fenestrations 135 may be distributed along a length of the suction tube 130 within the porous medium 140, so that suction is applied to the porous medium 140 along its length. The fenestrations 135 may be sized, shaped and/or located to provide sufficient flexibility to the suction tube 130. The arrangement of fenestrations 135 may be selected to provide an even (e.g. uniform) distribution of suction at different positions of the porous medium 140 (e.g. as opposed to suction only being provided at the tip of the suction tube 130). This may enable a more uniform suction force to be applied within the defect, thereby providing a more uniform distribution of healing (drawing tissue towards the porous medium 140).

The arrangement of fenestrations 135 along the suction tube 130 may be selected so that the same, or a similar, amount of suction is provided at locations along the length of the suction tube 130. The cross-sectional area of fenestrations 135 may be selected based on the cross-sectional area of the suction tube 130, such as to inhibit suction being predominantly delivered to fenestrations 135 closer to the source of negative pressure. For example, the cross-sectional area of fenestrations 135 may increase the further down the suction tube 130 the fenestrations 135 are. The number or density of fenestrations 135 may also vary along the length of the suction tube 130. For example, the suction tube 130 may be arranged so that the cross-sectional area of fenestrations 135 per unit length of suction tube 130 increases from its proximal end to its distal end, so that fenestrations 135 at the proximal end do not use a disproportionately high amount of the suction (so suction is still provided at the distal end). The arrangement of fenestrations 135 on the suction tube 130 may be selected depending on a shape of the porous medium 140 (e.g. so that fenestrations 135 are adjacent regions to of the porous medium 140 with more material than other regions). For example, where the porous medium 140 may have a number of spokes extending radially outward, the fenestrations 135 may be located adjacent these spoked portions of the porous medium 140.

The porous medium 140 is arranged to be moved from a proximal position within the catheter 110 to a distal position outside the catheter 110. The porous medium 140 is configured so that it may be compressed to a volume which fits inside the catheter 110 and which may move within the catheter 110. For example, the porous medium 140 may be an open pore sponge, a mesh and/or a collagen sponge. The porous medium 140 may be capable of being unravelled, stretched out, or drawn out into a single thread of wire and which will return to its intended (e.g. normal, non-compressed) form when released. In the absence of constraints on the volume of the porous medium 140 (e.g. when it is no longer inside the catheter 110), it will adopt an expanded state having a larger volume (although in the example of a collagen sponge, the volume may remain constant, but it will still have been deployed distally out the end of the catheter 110 to a position for treatment). The porous medium 140 is configured to have a selected shape when in its expanded shape, and the porous medium 140 will adopt this selected shape when in its expanded shape, despite the shape it has when in a compressed state (inside the catheter 110). The porous medium 140 is configured to be of sufficient flexibility so that a catheter 110 housing the porous medium 140 may pass round bends in the body lumen of the patient.

The porous medium 140 is arranged to facilitate treatment of the defect internal of the human body by application of a negative pressure (e.g. providing suction) through the porous medium 140 at the defect. The porous medium 140 is configured so that a negative pressure applied along the length of its core (from the fenestrations 135 of the suction tube 130) will be transmitted to the surface of the porous medium 140. The device 100 may be configured so that suction is applied to the environment surrounding the porous medium 140. The porous medium 140 may be configured to facilitate tissue ingrowth for tissue in and around the defect. Tissue in the environment of the porous medium 140 may be drawn towards the porous medium 140 (due to the suction), and the porous medium 140 is configured to be biocompatible for tissue coming into contact therewith.

To prepare the device 100 for insertion into the patient, the suction tube 130 is inserted within the porous medium 140, and the inner tube 120 is connected to the suction tube 130. The porous medium 140 is compressed and inserted within the catheter 110. The catheter 110 may have a porous medium receiving section at its distal end where a ledge keeps the porous medium 140 in a fixed location in the catheter 110, and/or the catheter 110 may have a larger internal diameter in the porous medium receiving section. A portion of porous medium 140 may protrude out of the distal end of the catheter 110 to provide a softer leading edge for insertion into the body. The inner tube 120 and/or the catheter 110 is connected to a vacuum apparatus (e.g. at their respective proximal ends). The inner tube 120 and/or catheter 110 may be connected to the vacuum apparatus after the device has been inserted into the patient and the porous medium 140 has been deployed from the catheter 110 (e.g. to provide suction to the porous medium 140 using the vacuum apparatus, such as a vacuum pump). An outer surface of the catheter 110 may be lubricated.

In operation, the device 100 is inserted into an endoscope or affixed to the endoscope. The endoscope and device 100 are then inserted into the patient. In some examples, the device 100 may be inserted through a patient's nose and pulled back out through their mouth to be affixed to an endoscope and then moved to the intended location. For treatment of defects in the upper gastrointestinal tract, the device 100 will be inserted into the patient's nose or mouth. The device 100 may be passed through the patient's nose then out their mouth prior to insertion into an endoscope, or the device 100 may be inserted through the patient's mouth (e.g. in an endoscope). The pair may then be guided (e.g. under endoscopic visualisation) through the patient's gastrointestinal tract towards the defect. Depending on the size and/or location of the defect, the device 100 will be inserted either into the defect, or to a location proximal to the defect (close enough so that the porous medium 140 may be delivered from the catheter 110 and into the defect). The endoscope may remain inside the patient's gastrointestinal tract to facilitate insertion of the porous medium 140 into the defect (e.g. the endoscope may be removed once the porous medium 140 is arranged in the correct location in the defect). This may enable a physician to observe deployment of the porous medium to ensure it is in the correct location, and/or this may also help to hold the distal end of the catheter steady during deployment. A vacuum may then be applied to the porous medium 140. For example, once vacuum is applied to the porous medium 140 (and the catheter is no longer gripped by the endoscope, e.g. any endoscopic graspers or sutures have been released from gripping the catheter and returned into the endoscope), the endoscope may be removed. The vacuum may help hold the porous medium 140 in place while the endoscope is removed.

Once the device 100 is located at the desired location, the porous medium 140 is moved out of the catheter 110. As mentioned above, a portion of porous medium 140 may already extend out the distal end of the catheter for providing a soft leading edge for the device. Further moving the porous medium 140 out of the distal end of the catheter 110 involves controlling movement of the suction tube 130 by moving either the tube itself, or a component connected to the tube. This movement will be controlled from a location outside the patient, such as by pushing a proximal end of the inner tube 120. The porous medium 140 is then pushed out of the catheter 110, where it begins to expand to its selected shape at its uncompressed volume. A physician may control the amount of porous medium 140 which is moved out of the distal end of the catheter 110. For example, the volume deployed may be selected based on a cavity size. The device 100 is arranged to deliver negative pressure to the porous medium 140 irrespective of how far (or how much of) the porous medium 140 is deployed from the catheter 110.

The porous medium 140 will then typically be in the defect to be treated. In the event that the porous medium 140 is not deployed into the correct location, then it may be moved to its intended location inside the defect. For example, the porous medium 140 may be retracted back into the catheter 110 to facilitate relocation of the porous medium

140 (and e.g. to prevent the porous medium 140 obstructing the view from the endoscope). Once at the intended location, negative pressure is applied from the vacuum apparatus. This negative pressure is effectively transmitted through the inner tube 120/catheter 110 to the suction tube 130 and through the fenestrations 135. This negative pressure may also be transmitted to a hole at the distal end of the suction tube (if there is one—in some examples there will not be) to provide suction at the porous medium 140, and in its surrounding environment. This suction draws in tissue in the region surrounding the defect, to help heal the defect. In particular, any dead space of the cavity will be closed, as the defect is drawn into the porous medium. Any substances (e.g. sepsis) in this region will be drained from the cavity, and in particular this will help drain sepsis. The device may also provide improved source control, e.g. to prevent further leakage into the cavity. The device 100 may also facilitate tissue granulation and and/or promote healing. Any material passed through the porous medium 140 and into the suction tube 130 will also be drawn up through the inner tube 120/catheter 110 and out the patient.

After a selected amount of time has passed (typically 48 to 72 hours), the device 100 will be removed from the patient. For this, suction is stopped. The porous medium 140 will be retracted, such as by pulling at a proximal end of the inner tube 120. The porous medium 140 will be pulled out the leak cavity by pulling the entire device 100 proximally, e.g. by pulling the catheter 110 and the inner tube 120, such as at their proximal end. The wire or suture connecting the inner tube 120/suction tube 130 to the tip region of the porous medium 140 may facilitate a more uniform distribution of the pulling force to the different regions of the porous medium 140. This may enable the porous medium 140 to be pulled more cleanly out from the defect. For example, some tissue ingrowth may occur into the porous medium 140 which may make it harder to pull out the porous medium 140. A solution may be flushed through the catheter 110 and inner tube 120, such as saline, which may help separate any ingrown tissue from the porous medium. Once the porous medium 140 has been removed from the cavity, it may be retracted back into the catheter 110. The tapered distal end of the catheter 110 may facilitate re-compression of the porous medium 140 for reinsertion into the catheter 110. Once the porous medium 140 is back in the catheter 110, the catheter 110 is retracted from the patient.

Embodiments of the present disclosure may utilise selected shapes for the porous medium 140 to facilitate easier insertion of a catheter 110 containing the porous medium 140 and/or for improved treatment of the defect when the porous medium 140 is inserted. FIGS. 2*a* to 2*r* show exemplary shapes for the porous medium 140. These shapes shown correspond to the shape that the porous medium 140 will adopt when in its expanded configuration. It is to be appreciated in the context of the present disclosure that some of these shapes may appear different when compressed and inserted into a catheter 110. All of the shapes shown will provide a volume of porous medium 140 which is less than that of a cylinder having a constant diameter corresponding to the equivalent diameter of the porous medium 140 shown (e.g. the equivalent diameter that would be present if the shape were to be a circle). While the volume of porous medium 140 may be less than that of a cylinder with a constant diameter, the porous medium 140 may have an increased surface area as compared to that cylinder with constant diameter. It is to be appreciated in the context of the present disclosure that while the figures show a volume of porous material removed, these regions could instead have porous medium 140 which is of greater flexibility (e.g. is less dense) than other regions of the porous medium 140. The porous medium 140 may have a shape with voids (e.g. regions with no porous medium, or with less dense porous medium). The porous medium 140 may have smooth sides and/or curved ends. The porous medium 140 may be free from dangling bits or loose material at its edges.

As shown in FIGS. 2*a* to 2*d*, the shape may have a complete circular outer perimeter. That is, an outer volume for the porous medium 140 will be cylindrical, but the total volume of porous medium 140 will be less than that of the outer volume due to removed regions of porous medium 140 within the outer perimeter. As shown, the porous medium 140 has a hollow passageway 142 running along its longitudinal axis (e.g. through the core of the porous medium 140). The porous medium 140 also has an outer perimeter 144. The outer perimeter 144 is circular. Within the outer perimeter 144 there are a plurality of compression segments 148 (also referred to as separation regions or voids). Compression segments may separate two regions of porous medium 140. The volume of the compression segments 148 (e.g. the volume of separation between two adjacent regions of porous medium 140) are bigger than the pore size of the porous medium 140.

As shown in FIGS. 2*a* to 2*d*, the shape of the porous medium 140 may include a plurality of spokes 146. The spokes 146 may comprise regions of porous medium 140 which extend in a radial direction (e.g. axially outward), and which are adjacent to compression segments 148. The spokes 146 may connect an inner core region of the porous medium 140 (a region surrounding the hollow passageway 142) to the outer perimeter 144. The arrangement of the spokes 146 and the compression segments 148 is selected to enable increased radial compression of the porous medium 140 and/or to facilitate bending of the porous medium 140 (e.g. in a direction perpendicular to its longitudinal axis). The spokes 146 may have flared edges. The spokes 146 may be curved and/or straight, and/or may have smooth edges. The edges of the spokes 146 may have no dangling material (e.g. they may be clean cut).

In FIG. 2*a*, both the spokes 146 and the compression segments 148 are arcuate, e.g. they follow a curved trajectory from the inner core of the porous medium 140 to the outer perimeter 144. In FIG. 2*a*, the compression segments 148 and the spokes 146 are of a similar thickness. In FIG. 2*b*, the spokes 146 are straight. The compression segments 148 of FIG. 2*b* have straight edges, but with the inner and outer radial regions (adjacent the core region and the outer perimeter 144) being curved, e.g. to conform to the circular shape thereat. In FIG. 2*b*, the spokes 146 do not extend directly radially out, but they are at an angle to the radial direction. As shown, the compression segments 148 may be of larger cross-sectional area than the spokes 146 (e.g. they may be thicker than the spokes 146). FIG. 2*c* shows the porous medium 140 with curved compression segments 148, and spokes 146 that extend straight outwards (but not directly radial). FIG. 2*d* shows the porous medium 140 with wider spokes 146 which extend directly radially outward.

As shown, the porous medium 140 of FIGS. 2*a* to 2*d* may have an inner perimeter (e.g. circular) which surrounds the hollow passageway 142, and an outer perimeter 144 (e.g. circular). The outer perimeter 144 may encompass the rest of the porous medium 140 (and the compression segments 148). The inner perimeter may encompass the hollow passageway 142. The spokes 146 may extend from the inner perimeter to the outer perimeter 144. The compression segments 148 may separate adjacent spokes 146 (and they too may extend from inner perimeter to outer perimeter 144). Both the spokes 146 and the compression segments 148 may have straight edges, or rounded edges. The spokes 146 may be of the same volume, or greater or lesser volume than the compression segments 148. The spokes 146 may extend directly radially outward (e.g. along the radial axis), or at an angle to the radial axis, or following a curved path. The arrangement of spokes 146 and compression segments 148 may be selected to provide a desired level of flexibility (e.g. perpendicular to the longitudinal axis—parallel to hollow passageway 142) and compressibility (along radial axis). The spokes 146 and/or compression segments 148 may be tapered along their length (e.g. narrower at one end than at the other end). For example, the spokes 146 may be narrower at their radial outermost end—this tapering may be continual along the length of the spoke, or in discrete sections which have different thicknesses. The porous medium of the present disclosure may have two or more spokes, such as three, four, five, six, seven or eight spokes, or even more than eight spokes.

Each of the spokes 146 and the compression segments 148 may have continuous or variable cross-sectional area along the length of the porous medium 140. For example, the same cross-sectional shape may be present at each cross-section perpendicular to the longitudinal axis along the length of the porous medium 140. In such examples, this volume of porous medium 140 may be removed from a whole cylinder (e.g. by gouging the porous medium 140 with a cutting device having a shape conforming to the shape of the compression segment). The cross-sectional shape may differ along its length. For example, the porous medium 140 may be made of a combination of different regions of porous medium 140 which are attached to one another. Each of the individual regions may have its compression regions cut (e.g. gouged) out.

FIGS. **2*e* and 2*f* show examples where the shape changes along the length of the porous medium 140. That is, at different regions along its length (its longitudinal axis), the shape of the porous medium 140 is different. That way, as compared to a cylinder of the same diameter (e.g. the maximum diameter at any point along the length of the porous medium 140), the porous medium 140 of FIGS. 2*e* and 2*f* will have less volume. In FIG. 2*e*, the porous medium 140 is tapered so that a first end of the porous medium 140 has a greater cross-sectional area than at the second end. The first end may correspond to a distal end or a proximal end of the porous medium 140. The taper may be a continuous one, or it may occur in discrete intervals. FIG. 2*f* shows a porous medium 140 having a plurality of repeating regions 149 where the cross-sectional area follows a repeating pattern which repeats along the length of the porous medium 140. For example, the repeating pattern may comprise a tapering in the repeating region, which is repeated a number of times along the length of the porous medium 140. The repeating regions 149 may provide a varying flexibility distribution along the length of the porous medium 140, so that in certain regions, the porous medium 140** has high flexibility, and in other regions there is less flexibility.

It is to be appreciated in the context of the present disclosure that the shape of the porous medium 140 may be selected based on the size and/or shape of defect to be treated. For example, the porous medium 140 may have a shape which is selected to conform to the shape of the defect. For example, the shape may not be symmetrical. Non-symmetrical porous medium 140 may find utility when only a portion (e.g. one side/half) of the porous medium 140 will actually be inserted into, or pressed against, the defect. Regions of the porous medium 140 which are to come into contact with the defect (or tissue in that region) may have rounded edges, such as to inhibit damage to the tissue from the porous medium 140. For example, the outermost regions of the porous medium 140 may have smooth and/or curved (e.g. rounded) surfaces.

FIGS. **2*g* to 2*r* show porous medium 140 shapes where there is no continuous circular outer perimeter 144. Each of these shapes has a plurality of radially extending spokes 146. The spokes 146 may have rounded edges. The spokes 146 may be tapered, e.g. so that they are wider closer to the hollow passageway 142 that at their radial tip. The porous medium 140 may have two or more spokes 146, such as three or more spokes 146 or four or more spokes 146. The shapes may be symmetrical, or not. The spokes 146 may extend directly radially outward, or at an angle to directly radially outward. All of these shapes may be formed by cutting away material from a larger portion of porous medium 140, such as a cylinder having a diameter corresponding to (e.g. the same as) the spoke length of the spokes 146. In these examples, the compression segments 148 may be considered to be the segments which are missing from a circular cross-section for the shape (e.g. the segments required to be filled in to provide a solid circle with the spoke diameter as the diameter of the circle). The spokes 146 may be of sufficient flexibility that they may be compressed, e.g. folded, or curled up, for insertion into the catheter 110 (e.g. they may be bent round to fill in empty space adjacent to the spokes 146). The spokes 146 may have flared edges. The spokes 146 may be curved and/or straight, and/or may have smooth edges. The edges of the spokes 146** may have no dangling material (e.g. they may be clean cut).

FIGS. **2*g*, 2*h*, 2*l* and 2*m* show examples of shapes where the spokes 146 increase in thickness along a region extending radially outwards. FIGS. 2*i*, 2*k*, 2*o*, 2*p* and 2*r* show shapes where the spokes 146 have the same thickness along a region extending radially outwards. A number of the other figures show shapes where, at least in some region of the spokes 146 extending radially outwards, the width of the spokes 146** decreases. The shapes may have a combination of these profiles, so that they may have a width which remains the same, increases and/or decreases along the radial direction (moving outwards).

FIGS. **2*g* and 2*h* each show a five-spoked shape. In both cases, the spokes 146 have curved tips. The tips follow the curve of a circular cross-section. The spokes 146 may have a thinner width closer to the core of the shape, e.g. the thinnest region of each spoke is that closest to the inner core of the porous medium 140. From this inner region of the spoke, the spoke widens up to a more radially outward region, where the width of the spoke corresponds to the circular shape. In FIG. 2*g*, the spokes 146 are symmetrical and extend directly radial outward. In FIG. 2*h*, the spokes 146** are curved and extend at an angle to directly radially outward.

FIGS. **2*i*, 2*j*, 2*k* and 2*l* each show a five-spoked star-like shape. As with FIGS. 2*g* and 2*h*, in FIGS. 2*i* to 2*l*, the spokes 146 are distributed uniformly about the shape (e.g. the angle separating each spoke from its adjacent spoke is the same for all spokes 146). FIGS. 2*j* and 2*l* show shapes having spokes 146 with rounded tips, whereas FIGS. 2*i* and 2*k* show shapes having flat (or less rounded) tips. In FIG. 2*i*, the width of each spoke is relatively constant along its radial length (e.g. it is either flat or narrows slightly). In FIG. 2*j*, each spoke tapers so that its width decreases along its radial length. The taper is consistent. The width of each spoke decreases uniformly along its length so that it is widest proximal to the core region of the porous medium 140. The shape of FIG. 2***j* is star-shaped. In FIG. 2*k*, the width of each spokes 146 is the same along its length (or decreases slightly as it extends radially outward). The spokes 146 of FIG. 2*j* extend radially outward at an angle to the radial direction (e.g. they do not extend directly radially outward). In FIG. 2*l*, the spokes 146 have a width which increases, stays the same and decreases at different regions along the radially extending length. As shown, each spoke initially tapers outwards (so that it gets wider with increased radial distance). The spokes 146 then transition into a decreasing width taper (via a flat region). In other words, the outer surface of the spokes 146 follows an arcuate profile (e.g. each side of the spokes 146 is arcuate). The transition between each spoke (at the inner region of the shape) may be either a straight line or curved.

FIGS. 2*m* to 2*p* each show a three-spoked shape. The spokes 146 are distributed uniformly about the hollow passageway 142 (e.g. they are each 120 degrees apart from one another). Each spoke is connected to its adjacent spoke at the inner region of the porous medium 140. The connection between adjacent spokes 146 is either a straight line/vertex or a curved trajectory between spokes 146. Each spoke may have a flat tip or a curved tip. The spokes 146 may have regions where their width remains constant along the radial axis, and/or regions where the width increases/decreases. The thickness of the spokes 146 and/or the separation between adjacent spokes 146 may be selected to enable the spokes 146 to be bent round into the space between adjacent spokes 146 (e.g. the spokes 146 may be radially compressible into space between the spokes 146).

FIG. 2*m* shows a three-spoked shape where each spoke has an arcuate profile, e.g. so that the width of each spoke increases and decreases at different regions. As the spoke extends outwards, it gets fatter, before thinning to have a rounded tip. FIG. 2*n* shows a three-spoked shape where there is a smooth region connecting each spoke (e.g. so that the cross-section arcs between adjacent spokes 146). Each individual spoke in FIG. 2*n* is tapered so that its width decreases with increased distance away from the core. The spokes 146 have rounded tips. FIG. 2*o* is similar to the shape of FIG. 2*n*, but in FIG. 2*o* each spoke has a region where its width remains constant as it extends outwards radially, before the width then decreasing as the tip rounds. FIG. 2*p* is similar to FIG. 2*o*, but it has wider spokes 146. Also, the region of the spokes 146 with constant width is smaller in FIG. 2*p*.

FIGS. 2*q* and 2*r* each show a four-spoked shape. The spokes 146 are distributed evenly about the shape. In both FIGS. the spokes 146 have rounded tips. In FIG. 2*q*, each spoke has an arcuate cross-section. Each spoke is tapered so that it is wider close to its core. The shape of FIG. 2*r* is similar to that of FIG. 2*q*, but each spoke has a region where its width remains constant as it extends radially outward.

The arrangement of fenestrations 135 on the suction tube 130 may be selected depending on a shape of the porous medium 140. The location of at least some (e.g. all) of the fenestrations 135 may correspond to the location of the regions of the porous medium 140 which have more material extending therefrom. For example, where the porous medium 140 has spokes 146, the fenestrations 135 may be located so that they are proximal to the spokes 146 (e.g. so that the fenestrations 135 and spokes 146 are at least partially aligned with one another). The fenestrations 135 may be arranged so that suction provided through the fenestrations 135 may be transmitted through as much porous medium 140 as possible (e.g. rather than passing into compression segments 148 of the porous medium 140). For example, the fenestrations 135 may be located in columns, so that each column of fenestrations 135 corresponds to a radial position of a spoke of the porous medium 140 (e.g. there may be 3 or 4 or 5 or more columns of fenestrations 135 radially disposed about the suction tube 130). Each of said columns may or may not have the same number of rows of fenestrations 135, and/or the fenestrations 135 in each column may not have the same row position.

The examples described herein may provide a number of different advantageous effects. As one example, devices of the present disclosure may be made which have greater flexibility, and this may thus facilitate deployment. For example, the provision of a thinner wall portion for the catheter 110 at the distal end may reduce the stiffness of the material in that region and increase the flexibility. Similarly, the shapes for the porous medium 140 may enable a volume reduction in that material, while also providing a higher porous medium surface area (which may increase therapeutic benefit of the porous medium 140 once deployed). The reduction in the volume of the porous medium 140 at the distal end of the catheter 110 may also provide increased flexibility in that region.

Another advantage common to the examples described is that there may be a reduction in friction for movement of the porous medium 140 and/or inner tube 120 relative to the catheter 110 (e.g. movement of the porous medium 140/inner tube 120 inside the catheter 110).

For example, the spoked porous medium shapes may reduce the volume of porous medium in the distal end of the catheter. This may reduce the force exerted outwards from the porous medium to the catheter, as well as to decrease the contact surface area between the two and/or to reduce the porous medium stiffness in the contact region between the external surface of the porous medium and an internal surface of the catheter. This may provide a reduction in friction forces between the porous medium 140 and the catheter 110.

Similarly, the provision of an internal ledge may reduce friction forces between the porous medium 140 and the catheter 110. For example, a thinner distal end to the catheter 110 may provide a greater internal diameter in that region of the catheter 110, thereby decreasing the pressure that would be exerted from that material onto the porous medium in that region. As another example, the fenestrations in the core may enable a more balanced air flow to different regions (e.g. to avoid any unwanted pressure build ups), and this may reduce corresponding friction forces. These examples may also provide a reduction in friction forces between the porous medium 140 and the catheter 110.

As another example, the inclusion of a friction reducing lining/integration of a friction reducing material into an inner surface of the catheter 110 may also reduce friction between an outer surface of the inner tube 120 and an inner surface of the catheter 110. Similarly, a coating (e.g. silicon) may be applied to the inner tube 120 so that it may have reduced friction when it moves inside the catheter 110. The friction reducing lining and/or the coating for the suction tube may be provided in proximal regions of the catheter 110 (e.g. regions proximal to the region where the porous medium 140 is located, such as to inhibit this material moving into contact with the treatment area). The coating for the inner tube 120 may be cured onto the inner tube 120 (e.g. the inner tube may be formed of stainless steel, and a silicone coating may be cured thereon). These examples may provide a reduction in friction forces between the inner tube 120 and the catheter 110.

In other words, the technology described herein may enable easier deployment and/or retraction of the porous medium 140 relative to the catheter 110. That is, the technology may provide a reduction in friction for movement of the porous medium 140 relative to the internal surface of the catheter 110, and/or a reduction in friction for movement of the suction tube 120 relative to the internal surface of the catheter 110. This may include movement associated with deployment of the porous medium (e.g. distal movement of the porous medium relative to the catheter, such as to move the porous medium away from the catheter for placing it in, or near to, a defect), and/or movement associated with retraction of the porous medium (e.g. proximal movement of the porous medium relative to the catheter, such as to bring the porous medium back into the catheter for re-deployment or removal from the body).

By making this relative movement of the porous medium/suction tube relative to the catheter easier (e.g. by reducing friction), the forces required for deployment/retraction may be reduced, and also the deployment and/or retraction may be controlled with greater precision.

To facilitate such deployment and/or retraction of the porous medium, vacuum therapy devices of the present disclosure may be provided in combination with a deployment applicator for controlling deployment and/or retraction of the porous medium. As the vacuum therapy devices of the present disclosure may have much reduced friction associated with movement of the inner tube relative to the catheter, a simpler, hand-held device may be used to provide controlled deployment. For example, the vacuum therapy device designs of the present disclosure may enable a deployment applicator which is hand-held, and operable with only one hand to be used to provide all necessary force to deploy the porous medium.

An example of such a deployment applicator will now be described with reference to FIGS. 3*a* and 3*b*.

Figure 3A:
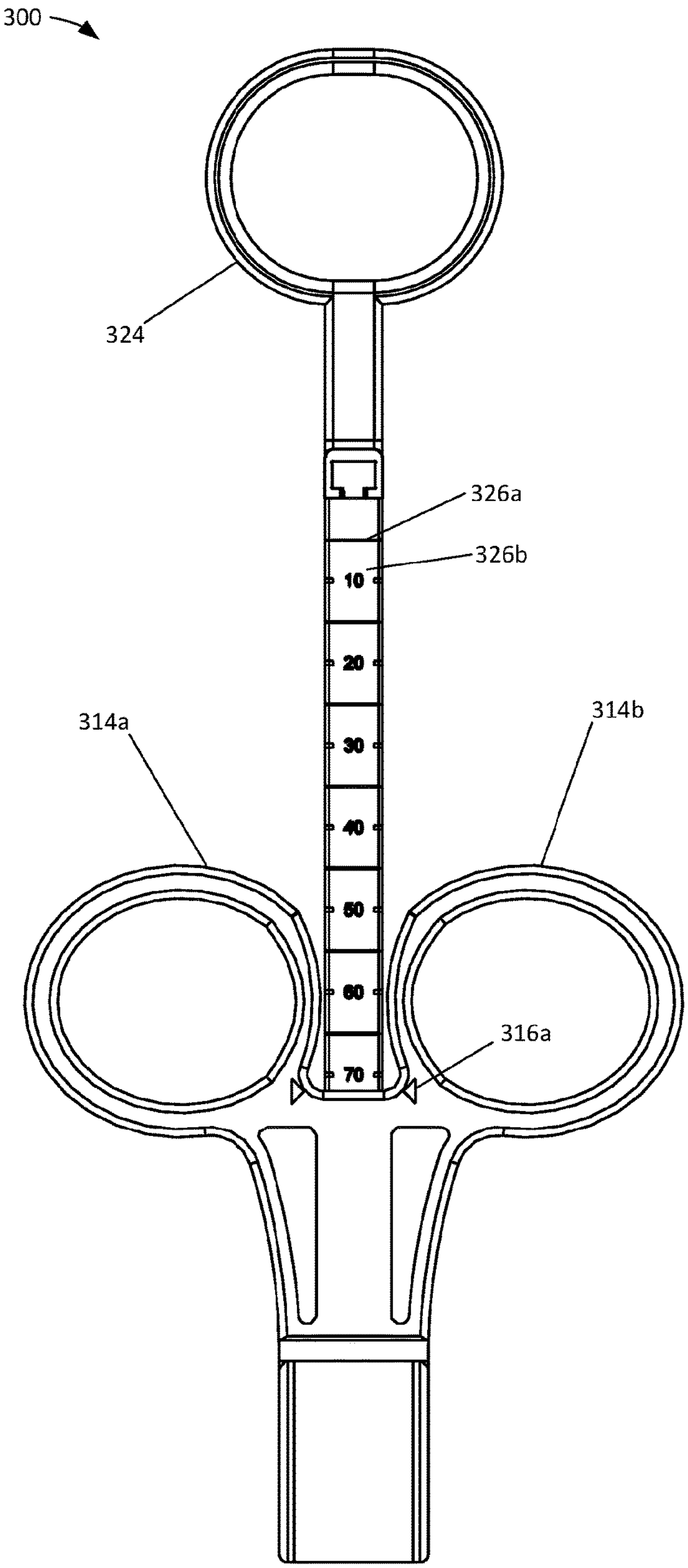
Figure 3B:
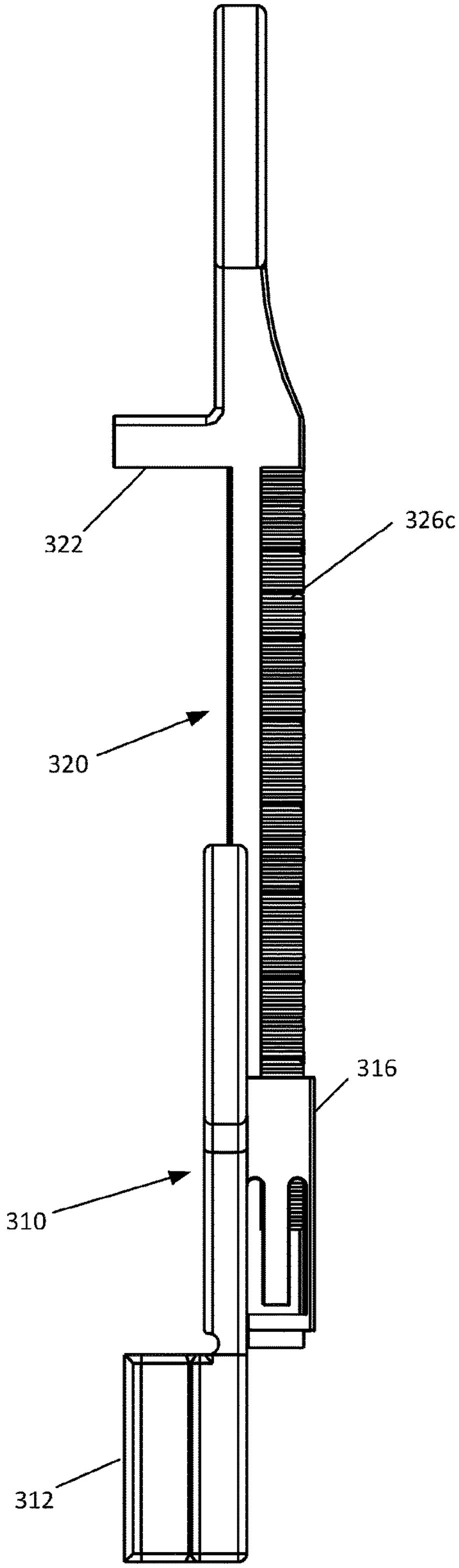

FIGS. 3*a* and 3*b* show a deployment applicator 300. The deployment applicator 300 comprises a stationary portion 310 and a moving portion 320. The deployment applicator 300 is a hand-held device, e.g. for single-handed use. The applicator 300 includes a plurality of gripping regions for enabling a physician to manipulate and control the use of the device. The gripping regions may include a plurality of finger/thumb loops. In the example shown in FIG. 3*a*, the moving portion 320 includes a thumb loop 324. The stationary portion 310 includes two finger loops: first finger loop 314*a* and second finger loop 314*b*.

The stationary portion 310 includes a catheter coupling 312. The moving portion 320 includes a driving flange 322. Although not shown in the figures, a catheter 110 of a vacuum therapy device 100 may be coupled to the deployment applicator 300 at the catheter coupling 312 (and the catheter 110 will extend distally away from the catheter coupling 312 towards the distal end of the catheter 110). Also not shown in the figures is a movable element for coupling the driving flange 322 of the deployment applicator 300 to the inner tube 120 of the vacuum therapy device 100 (e.g. so that movement of the driving flange 322 relative to the catheter coupling 312 may cause a corresponding movement of the porous medium 140 relative to the catheter 110 by moving the inner tube 120, and thus porous medium 140, relative to the catheter 110).

The applicator 300 also includes a movement indicator mechanism for providing information and/or feedback relating to deployment/retraction of the porous medium. For this, a body of the moving portion 320 of the applicator 300 is arranged to interact with a receiving region 316 of the stationary portion 310 of the applicator 300. The body of the moving portion 320 includes one or more features for providing information and/or feedback about deployment/retraction. This may include measurement lines 326*a* and/or corresponding measurement indicia 326*b*, as well as a textured surface 326*c*. The receiving region 316 of the stationary portion 310 of the applicator 300 may include a measurement indicator 316*a*, which is arranged for interaction with the measurement lines 326*a* and/or measurement indicia 326*b* of the moving portion 320. Although not shown, the receiving region 316 may also include an interaction surface for interacting with the textured surface 326*c* of the body of the moving portion 320.

The applicator 300 is provided as a two-piece construction. The features of the moving portion 320 are integrated into one single component (e.g. they may be made from the same piece of material). Similarly, the features of the stationary portion 310 are integrated into another single component.

The stationary portion 310 extends from the catheter coupling 312 at its distal end up to the two finger loops 314*a*, 314*b* at its proximal end. The catheter coupling 312 defines an internal channel into which a catheter 110 of a vacuum therapy device 100 is to be inserted. The channel extends distally until the end of the stationary portion 310. Although not shown, the coupling may include a clamp for clamping a catheter 110 in the coupling to hold it in a fixed position. The finger loops 314*a*, 314*b* are oval shaped. The finger loops 314*a*, 314*b* are located in a region of the stationary portion 310 which is proximate to the thumb loop 324 of the moving portion 320 (e.g. the finger loops 314*a*, 314*b* are located on the side of the stationary portion 310 which is closer to the thumb loop 324 of the movable portion). Each finger loop is formed of an outer rim of material surrounding (e.g. circumscribing) an aperture. The first and second finger loops 314*a*, 314*b* are sized and shaped based on index and middle fingers for an adult human. The two are also spaced apart based on spacing between index and middle fingers for an adult human. The finger loops 314*a*, 314*b* are aligned with an edge (e.g. a wall) of the catheter coupling 312 (e.g. they extend up from the wall in a straight line). The stationary portion 310 may include one or more holes where material has been removed.

The measurement indicator 316*a* is located between the finger loops 314*a*, 314*b*. The measurement indicator 316*a* comprises one or more arrows aligned with an edge of the stationary portion 310. The edge is straight and runs perpendicular to the direction of the internal channel of the catheter coupling 312. As shown, the indicator may comprise one arrow on either side of the edge, where the arrows point towards the edge. The receiving region 316 is arranged between the finger loops 314*a*, 314*b* and the catheter coupling 312. The receiving region 316 is arranged on the other side to the catheter coupling 312 (e.g. so that the region between the internal channel of the catheter coupling 312 and the driving flange 322 remains unobstructed). The receiving region 316 is shaped to include a receiving channel into which the body of the moving portion 320 may move. The receiving channel is shaped so that the body of the moving portion 320 fits snugly inside the receiving channel. The receiving channel is open at its proximal end (for receiving the body of the moving portion 320), and it may be open at its distal end (so the distal end of the body of the moving portion 320 may move through the channel and out the distal end).

The thumb loop 324 is located at the proximal end of the moving portion 320. The thumb loop 324 is oval shaped.

The thumb loop 324 is formed of an outer rim of material surrounding (e.g. circumscribing) an aperture. The thumb loop 324 is sized and shaped based on a thumb for an adult human. The thumb loop 324 is aligned with the body of the moving portion 320. The body of the moving portion 320 extends distally away from the thumb loop 324. The body extends away in a straight line from the thumb loop 324. The textured surface 326*c* covers the majority of one surface of the body (e.g. along the length of the body). The measurement lines 326*a* and indicia 326*b* may be provided on another surface of the body, and they may extend along a majority of that surface of the body (e.g. along its length). The measurement lines 326*a* may be spaced apart from each other by a selected distance, and the measurement indicia 326*b* may provide an indication of that distance. For example, each line may be 10 mm away from the next line in the distal direction, and each indicia 326*b* may indicated how many mms that line is away from a proximal or distal-most line.

The thumb loop 324 and/or driving flange 322 are located above the finger loops 314*a*, 314*b*. The thumb loop 324 may be positioned directly above the finger loops 314*a*, 314*b*. For example, the thumb loop 324 and the finger loops 314*a*, 314*b* may be parallel with each other (e.g. so that a force applied to the thumb loop for deploying the porous medium will be directed towards the finger loops, where an opposite force may be applied, also for deploying the porous medium, and vice-versa). The finger loops 314*a*, 314*b* may be located either side of the body of the moving portion 320 (e.g. they may be distributed symmetrically about that body). The driving flange 322 extends outwards from the body of the applicator 300. The driving flange 322 is aligned with the internal channel of the catheter coupling 312. For example, the movable element may extend in a straight line (distally) from the driving flange 322 and into the internal channel of the catheter coupling 312. The driving flange 322 will abut the movable element and hold it in a fixed position relative to the flange. Movement of the moving portion 320 (and thus the driving flange 322) in either direction (deploy or retract) will cause a corresponding movement of the movable element in either a distal or proximal direction.

The moving portion 320 is installed relative to the stationary portion 310 so that at least a portion of the body of the moving portion 320 extends through the receiving channel of the receiving region 316 of the stationary portion 310. The moving portion 320 may be movable between a maximally retracted position, with the driving flange 322 furthest away from the catheter coupling 312, and a maximally deployed position, with the driving flange 322 closest to the catheter coupling 312. In the maximally retracted position, the thumb loop 324 is furthest away from the finger loops 314*a*, 314*b*. In the maximally retracted position, the majority of the length of the body of the moving portion 320 may separate the thumb loop 324 from the finger loops 314*a*, 314*b*. As the thumb loop 324 is pushed distally (towards the maximally deployed position), the thumb loop 324 is brought closer to the finger loops 314*a*, 314*b*. In the maximally retracted position, the thumb loop 324 may be separated from the two finger loops 314*a*, 314*b* by a distance less than the maximum amount of separation between thumb and index and middle fingers of an adult human hand (e.g. so that an average adult human will not have to stretch their hand to the greatest extent to reach all three holes). For example, a distance of separation between the finger loops 314*a*, 314*b* and the thumb loop 324 may be under 20 cm, such as under 15 cm, e.g. under 12 cm, when in the maximally retracted position. A distance of separation between the finger loops 314*a*, 314*b* and the thumb loop 324 may be at least 2 cm, such as at least 5 cm when in the maximally retracted position. For example, movement between the maximally retracted and the maximally deployed position may be at least 2 cm, such as at least 5 cm (e.g. to provide a corresponding deployment of the porous medium). The device may be arranged so that movement of the porous medium between insertion and deployment positions is in the region of 6 cm (e.g. the porous medium will move 6 cm relative to the catheter for deployment). The separation between finger and thumb loops may be more than 6 cm, e.g. between 7 and 12 cm.

The thumb and finger loops are aligned with each other, e.g. the thumb loop may be arranged to be in the same plane as the finger loops (but above them). When looking front on, there may be a gap between the two finger loops. The finger loops may be parallel with each other (and they may be symmetric about the gap). The thumb loop may be aligned with that gap between the finger loops, but located above it. The three loops may be in the same plane (e.g. there may be no offset between them when looking side on). For example, a force applied to the thumb loop for deployment may be in the same plane as the finger loops (e.g. they may be parallel with each other with no offset when viewed side on).

The thumb loop 324 may be arranged with only a small offset to the flange when viewed side on. For example, at least a portion of the material which provides the thumb loop 324 may overlie (e.g. have no offset from) a portion of the material which provides one or both the finger loops 314*a*, 314*b*). In other words, the applicator 300 is arranged so that a distal (e.g. downward) force applied to the thumb loop 324 is also applied distally through the flange for pushing the movable element towards the catheter coupling 312. The finger loops 314*a*, 314*b* may be pulled to provide a force in the opposite direction (e.g. so as to bring the thumb loop 324 towards the finger loops 314*a*, 314*b*, and thus the flange towards the catheter coupling 312 for pushing the movable element into the catheter 110 (for pushing the porous medium distally relative to the catheter 110). The body of the moving portion 320 may extend in the opposite direction to the flange (e.g. it may taper outwards). For example, the body may then interact with the receiving region 316 of the stationary portion 310 at a position which is offset from the loops/flange.

The applicator 300 is arranged to control deployment of the porous medium relative to the catheter 110. The moving portion 320 is arranged to be movable relative to the stationary portion 310. For example, the body of the moving portion 320 may be slidably received in the receiving region 316 of the stationary portion 310. The moving portion 320 may be arranged so that it may slide proximally and/or distally relative to the stationary portion 310 (e.g. a portion of the body may move proximally and/or distally within the receiving channel of the stationary portion 310).

The catheter coupling 312 is arranged to hold the catheter 110 in a fixed position. For example, the catheter coupling 312 may comprise a locking and/or clamping mechanism arranged to secure the coupling to the catheter 110 so that movement of the catheter 110 relative to the catheter coupling 312 is inhibited.

The movable element of the applicator 300 is arranged to couple the driving flange 322 to the inner tube 120 inside the catheter 110. The movable element may be arranged to couple to the driving flange 322 and the inner tube 120 so that those components move together (e.g. to inhibit any relative movement between those components). For example, the movable element may be coupled to the flange so that movement of the flange (i.e. movement of the movable portion) in either direction will also cause the movable element to move in either direction accordingly. Similarly, the movable element may be coupled to the inner tube so that this movement of the moving portion, and thus the corresponding movement of the movable element, causes the inner tube to move accordingly (e.g. proximally or distally).

The movable element may be arranged to couple to the inner tube in a detachable way. In particular, the movable element may be arranged to be coupled with the inner tube during the deployment process (optionally this may include any retraction used during the deployment process, such as for repositioning the porous medium). Once the porous medium is deployed, the movable element may be detached from the inner tube (e.g. uncoupled thereto), so that a vacuum device may be coupled to the inner tube (for providing suction thereto).

At least one of the inner tube and the movable element may comprise detachable coupling means for coupling the two together (e.g. to enable bidirectional movement of the two together). Each component may have a corresponding portion designed for engagement with the other. For example, the two devices may have mating means which, when selectively engaged with each other, inhibit relative motion of one component relative to the other. Those mating means may also be selectively disengaged to enable removal of the movable element from the inner tube. Any suitable coupling means may be provided for this. For example, the coupling means of one of the inner tube or movable element may be arranged to grasp, secure to and/or fit within a corresponding component of the other one. For example, the movable element may comprise a lug arranged to fit in a mating slot feature of the inner tube (e.g. a T-slot). A corresponding movement (e.g. a rotation) of the coupling means may act to engage or disengage the coupling (e.g. to select whether relative movement is permitted or inhibited). The movable element may also be arranged to couple to the flange in a detachable way (e.g. in a similar manner to that described above in relation to the inner tube).

The moving portion 320 is arranged to couple to the inner tube 120 of the vacuum therapy device 100 and the stationary portion 310 is arranged to couple to the catheter 110 of the vacuum therapy device 100, so that movement of the moving portion 320 relative to the stationary portion 310 provides movement of the porous medium relative to the catheter 110. The movement of the moving portion 320 may provide a corresponding movement of the porous medium. For example, the applicator 300 may be arranged so that distal movement of the moving portion 320 relative to the stationary portion 310 (e.g. pushing the thumb loop 324 towards the catheter coupling 312) will cause a corresponding distal movement of the porous medium relative to the catheter 110 (e.g. movement of the porous medium out of the distal end of the catheter 110, and optionally further distally away therefrom). For example, the applicator 300 may be arranged so that proximal movement of the moving portion 320 relative to the stationary portion 310 (e.g. pulling the thumb loop 324 away from the catheter coupling 312) will cause a corresponding proximal movement of the porous medium relative to the catheter 110 (e.g. movement of the porous medium back into the catheter 110 from outside the catheter 110).

The deployment applicator 300 is arranged to provide controlled deployment and/or retraction of the porous medium relative to the catheter 110. In particular, the applicator 300 itself may be manipulated so as to provide a desired movement (e.g. deployment/retraction) of the porous medium. The applicator 300 is arranged to provide user feedback for deployment and/or retraction of the porous medium. That is, the applicator 300 is arranged to provide one or more indications to the user as to how much deployment/retraction of the porous medium has occurred. For example, the applicator 300 may be arranged to provide at least one of: audible, tactile and/or visible feedback to a user. The applicator 300 may provide all three. Audible feedback may comprise the applicator 300 being arranged to provide a noise associated with movement of the moving portion 320 (e.g. movement of a selected distance). Tactile feedback may comprise the applicator 300 providing a feeling, e.g. a vibration, associated with movement of the moving portion 320 (e.g. movement of a selected distance). Visible feedback may comprise the applicator 300 being arranged to provide a visual display associated with movement of the moving portion 320 (e.g. to indicative an amount of distance through which the moving portion 320 has moved).

The body of the moving portion 320 may interact with the receiving region 316 of the stationary portion 310 to provide feedback. For example, the applicator 300 may be arranged so that movement of the moving portion 320 causes the textured surface **326*c* of the body to engage with a corresponding surface of the receiving region 316. The textured surface 326*c* may comprise one or more ridges which are arranged to engage with a corresponding portion of the receiving region 316. As the body moves through the receiving region 316, e.g. as the textured surface 326*c* slides past the corresponding portion of the receiving region 316, the ridges will bump over the portion of the receiving region 316 causing vibration of the device and/or an associated clicking noise. In other words, this may provide audible and/or tactile feedback associated with movement of the device. The textured surface 326*c* may have a series of grooves, each spaced a selected distance apart along the length of the body (e.g. 1 mm, 2 mm, 3 mm, 4 mm, or 5 mm). Each time the body is moved through that selected distance relative to the receiving region 316, the next groove will interact with the portion of the receiving region 316 to generate another noise and/or vibration. The portion of the receiving region 316** may comprise its own groove (or series of grooves).

The textured portion could comprise a series of protrusions (e.g. ridges) and/or recesses (e.g. valleys). The corresponding portion of the receiving region 316 may comprise one or more corresponding protrusions/recesses. Each time the body moves the selected distance through the receiving region 316, a next protrusion of the textured surface **326*c* may slide against and over a protrusion of the receiving region 316** causing the vibration and/or click. A user of the device may be able to identify based on touch and/or sound an indication of how far they have moved the device (e.g. how much deployment/retraction has occurred).

The measurement lines **326*a* and/or the measurement indicia 326*b* of the body of the moving portion 320 are arranged to interact with the measurement indicator 316*a* of the stationary portion 310 to provide visible feedback relating to movement of the moving portion 320 relative to the stationary portion 310. For example, the measurement indicator 316*a* may point towards a region on the stationary portion 310 of the applicator 300, and a measurement line and/or indicia 326*b* in the corresponding region of the moving portion 320 adjacent to said region of the stationary portion 310 may provide an indication of a deployment/retraction distance. For example, the measurement indicia 326*b* at the region on the body adjacent to the measurement indicator 316***a* may indicate how much further movement is still available (e.g. how much more the moving portion 320 can be moved for retraction and/or deployment, such as how much more movement until the applicator 300 reaches its maximal deployment or retraction position), or how much movement has already occurred (e.g. how much has the moving portion 320 already been moved, such as how much has it already moved from its maximal deployment or retraction position). The lines and/or indicia 326*b* may be spaced apart from each other by a selected distance (e.g. every 1 mm, e.g. every 2 mm, e.g. every 5 mm, e.g. every 10 mm).

As described above, the applicator 300 may be arranged so that the textured surface 326*c* comprises a series of ridges (and optionally corresponding valleys) arranged to slide over a corresponding textured portion of the receiving region 316 (e.g. which has its own ridge(s) and/or valley(s)). This engagement between the moving portion 320 and the stationary portion 310 may be arranged to permit two-way movement (e.g. for both retraction and deployment). The applicator 300 may be arranged to provide the audible and/or tactile feedback for motion in both directions.

Additionally, or alternatively, the applicator 300 may be arranged to provide one-way movement between the moving portion 320 and the stationary portion 310 of the applicator 300. For example, the receiving region 316 and the textured surface 326*c* may be arranged to provide a ratchet-type engagement. For this, the moving region may be operable to move in one direction relative to the receiving region 316, but movement of the moving region in the opposite direction is inhibited. For example, the deployment applicator 300 may be configured as a deployment-only applicator 300 (e.g. it may only be operated to provide deployment, rather than also retraction). The applicator 300 may be operable to disengage the one-way motion—for example, a portion of the receiving region 316 may be manipulated by the user (e.g. pulled away from the body of the moving portion 320) so that the textured surface 326*c* does not engage with the corresponding portion of the receiving region 316 to enable relative movement of the two in the opposite direction.

The applicator 300 may be a single-use component. For example, it may be disposable. The applicator 300 may be arranged to provide controlled deployment of the porous medium relative to the catheter 110. The applicator 300 may be removable from the vacuum therapy device 100, e.g. the catheter coupling 312 may be uncoupled from the catheter 110, and the movable element may be uncoupled from the inner tube 120 within the catheter 110.

In operation, as described above, the vacuum therapy device 100 is inserted into a patient. The device will be used to provide treatment to a defect, such as a cavity, inside the patient. The device may be inserted so that the distal portion of the catheter 110 is positioned in the defect, e.g. in a cavity, or near to the defect (e.g. so that the porous medium 140 may be deployed to the defect, e.g. into the cavity. For example, the device may be used for intraluminal vacuum therapy when the characteristics of the leak cavity are favourable. Alternatively, the defect may be a region of weakness, such as a surgical join, where there is no cavity, or a region of tissue surrounding a cavity. In such cases, the device will be inserted so that the distal end is near to the region to be treated. With the device inserted to the desired location, the distal end of the catheter 110 will be near to the defect. The porous medium will be mostly located within the catheter 110, but located at the distal end of the catheter 110.

The applicator 300 is coupled to the proximal end of the catheter 110 (either prior to the distal end of the catheter 110 being inserted into the patient, or afterwards once the distal end of the catheter 110 is in position). For this, the catheter coupling 312 is coupled to the catheter 110 of the device so that the catheter 110 is held in a fixed relationship relative to the catheter coupling 312. The movable element is coupled to the inner tube 120 of the vacuum therapy device 100. As described above, the movable element is also coupled to the driving flange 322 so that the two move together.

When ready to deploy the porous medium, the moving portion 320 is moved relative to the stationary portion 310 to effect this deployment. The thumb loop 324 is pushed towards the catheter coupling 312 (e.g. by pushing on the thumb loop 324 with the user's thumb and pulling on the finger loops 314*a*, 314*b* with the user's fingers). This causes the body of the moving element to slide through the receiving region 316 of the stationary portion 310. At the same time, the driving flange 322 is moved closer towards the catheter coupling 312 causing the movable element to push the inner tube 120 of the vacuum therapy device 100 further into the catheter 110, while the catheter coupling 312 holds the catheter 110 fixed (e.g. so that the movement of the moving portion 320 and driving flange 322 is just imparted into the inner tube 120). In turn, the porous medium at the distal end of the catheter 110 is also pushed distally relative to the catheter 110, and thus the porous medium is moved out from the catheter 110 towards the treatment region. A user of the device may control an amount of deployment based on audible, tactile and/or visible feedback received from the applicator 300 during deployment (e.g. by feeling/hearing vibrations as the textured surface 326*c* moves over a corresponding portion of the receiving region 316, and/or by viewing the measurement indicia 326*b*).

Once the porous medium is located at its desired location for treatment, the applicator 300 may be removed. For this, the catheter 110 and inner tube 120 may be clamped at a fixed location to prevent further deployment/retraction of the porous medium 140 while the applicator 300 is removed. The catheter coupling 312 may then be released to uncouple the applicator 300 from the catheter 110 (and the movable element may be uncoupled from the inner tube 120). The applicator 300 is then removed, and can be discarded. The source of negative pressure may then be coupled to the inner tube 120 for applying negative pressure to the defect via the deployed porous medium.

Figure 3C:
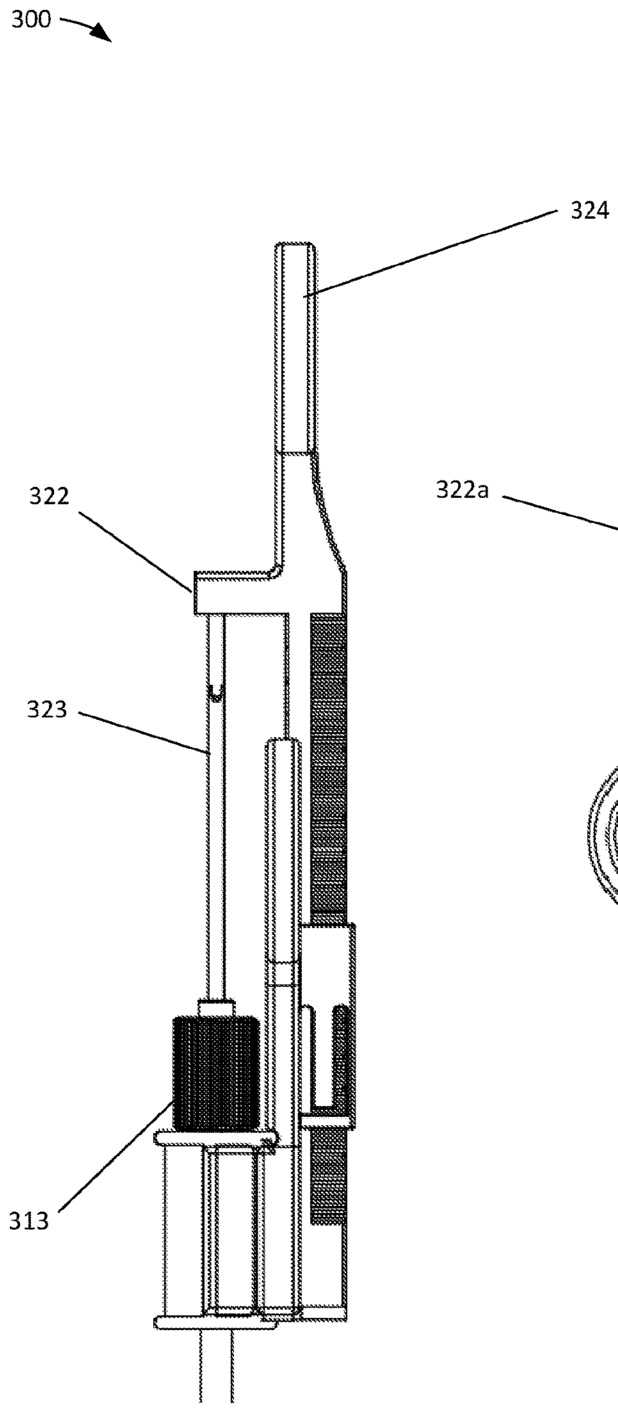
Figure 3D:
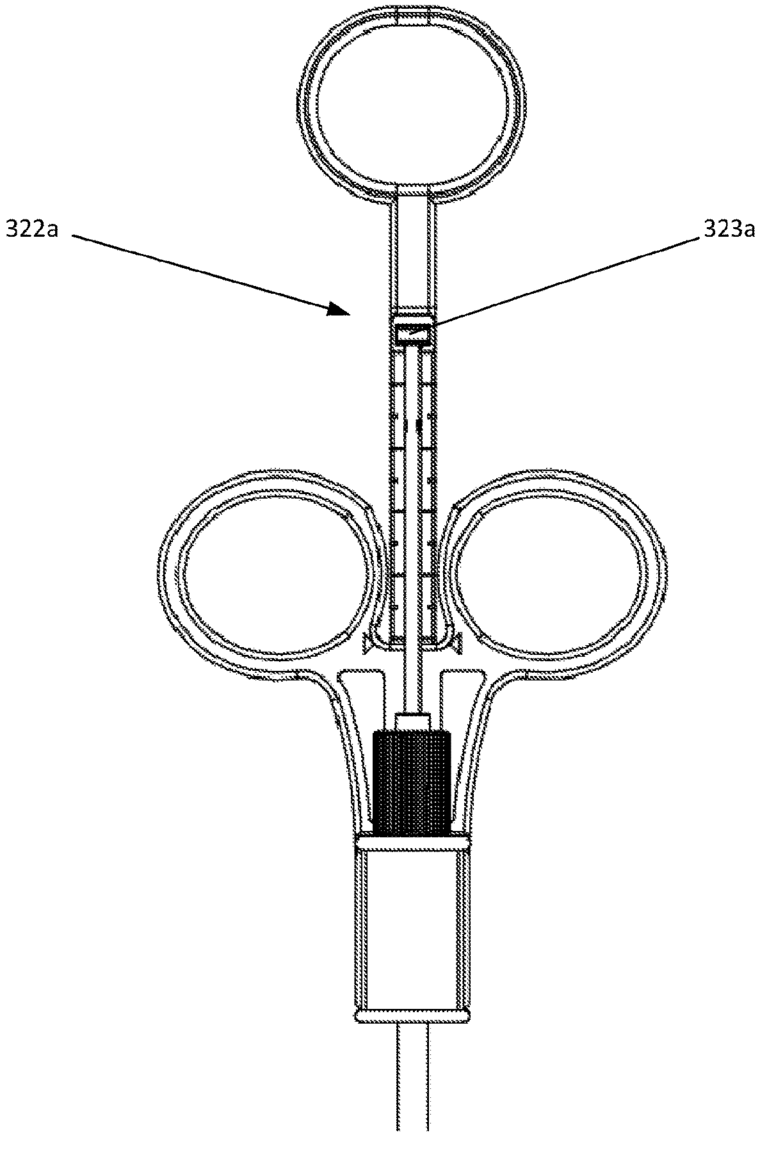

The method may also include retraction of the porous medium 140 back into the catheter 110. This may be performed during the deployment process—for example, if the deployment does not deliver the porous medium to the correct location, the porous medium may be retracted and then subsequently re-deployed. Additionally, or alternatively, a deployment applicator may be used for retraction of the porous medium at the end of the treatment so that the porous medium is back inside the catheter for removal from the patient. For this retraction, the thumb loop is moved in the opposite direction to for deployment (e.g. it is moved away from the finger loops). In turn, this will cause the flange to pull back the movable element, which will in turn pull back the inner tube, thus providing proximal movement of the porous medium 140 (e.g. bringing the porous medium 140 back towards the catheter 110). FIGS. 3*c* and 3*d* show the deployment applicator 300 with a few example additional features included. FIG. 3*c* shows a side on view of the applicator 300 and FIG. 3*d* shows a front on view.

In FIGS. 3*c* and 3*d*, a movable element is also included, shown as push rod 323. The push rod 323 is arranged to provide a rigid coupling between the flange 322 and the inner tube of the vacuum therapy device (as described above for the movable element). A proximal end of the push rod 323 is arranged to engage with a corresponding portion of the flange 322 (e.g. so that the two move together). As shown in FIG. 3*d*, the flange 322 includes a recess 322*a* and the push rod 323 includes a corresponding head 323*a*. The recess 322*a* is arranged to slidably receive the head 323*a*. With the head 323*a* inserted in the recess 322*a*, the head 323*a* is at least partially surrounded on proximal and distal sides by material of the flange 322. As such, movement of the flange 322 up (for retraction/proximal movement) or down (for deployment/distal movement) will cause a corresponding movement of the push rod 323. The recess 322*a* is open at one end to enable the head 323*a* of the push rod 323 to slide in and out of the recess 322*a*.

The head 323*a* may be inserted (slid) into the recess 322*a*. The other end of the rod 323 may be coupled to the inner tube. Movement of the flange 322 will cause a corresponding movement of the push rod 323 and thus porous medium. Once the porous medium is suitably deployed, the head 323*a* may be removed (slid out) from the recess 322. The distal end of the push rod 323 is uncoupled from the inner tube (e.g. by a rotation of the push rod 323 to disengage a coupling between the inner tube and the distal end of the push rod 323). The rod 323 may then be removed from the device and applicator.

Also shown in FIG. 3*c* is a vacuum coupling 313 for coupling the applicator to a source of negative pressure, such as a vacuum pump. Once the rod 323 has been removed, the vacuum source may be coupled to the vacuum therapy device (to provide the negative pressure) via the vacuum coupling 313.

It is to be appreciated that the above description of the deployment applicator 300 should not be considered limiting. For example, the arrangement of thumb loop 324 and finger loops 314*a*, 314*b* need not be considered limiting. This could be the other way round (e.g. finger loops on moving element), or there need not be two finger loops and one thumb loop—other number of loops could be used. Loops may not be used at all. Instead, the gripping region may comprise a region for fingers/thumbs to interact with, such as one or more ridges or protrusions designed to enable a user to apply pushing/pulling forces thereto. For example, the finger loops may be replaced by a bar-like structure which a user may place their fingers under for gripping. The thumb loop may be replaced by a structure which may be both pushed and pulled (e.g. which can be gripped on either side—one side for pushing, one side for pulling). The gripping regions may comprise one or more ridges/protrusions arranged to increase gripping for fingers/thumbs interacting therewith.

Similarly, the arrangement of the moving and stationary portion 310 need not be considered limiting. The applicator 300 is arranged to utilise relative movement of one portion relative to another to provide a corresponding movement of the porous medium relative to the catheter 110. However, the moving portion 320 may have finger loops, or could include the catheter coupling 312 for example. Similarly, a proximal end of the catheter may provide the stationary portion of the application (e.g. it may include one or more gripping regions, and may be coupled to the moving portion so that movement of the moving portion may occur relative to the catheter in response to pushing/pulling the moving portion, and holding the catheter in a fixed location using the one or more gripping portions thereof). Also, the applicator 300 described includes a movable element for coupling the driving flange 322 to the inner tube 120 of the vacuum therapy device 100, but it will be appreciated that any arrangement may be provided which may convert movement of the moving portion 320 into movement of the inner tube 120. For example, a portion of the body of the applicator 300 may be coupled to the inner tube 120 (e.g. without using a driving flange 322 and movable element). For example, the body of the moving portion 320 may be aligned with the catheter coupling 312 so that movement of a distal end of the body causes the movement of the inner tube 120).

While embodiments described herein have related to endoscopic vacuum therapy devices, embodiments of the present disclosure may find utility for other vacuum therapy devices for treatment of defects internal of a human or animal body. As another example, the catheter 110 may be introduced to a patient's body via percutaneous insertion, i.e. through the skin, similar to the method of inserting an intercostal chest drain, for example by performing a direct cut down, or using the 'Seldinger' technique. The catheter 110 may be used to perform percutaneous drainage, for example to treat an abscess in the peritoneal or pleural cavity, and the abdominal or thoracic cavity, in addition to being used to treat internal defects, such as leak cavities, as discussed above.

In examples where the device may be inserted percutaneously, the device may comprise one or more guidewires to facilitate insertion of the device to the correct location. The cavity may be needled first and accessed with a guidewire to enable the device to be railed into the cavity using the guidewire. In some examples, a sheath and/or dilator may be used to enable the insertion of the catheter 110 into the relevant location (e.g. cavity). It is to be appreciated in the context of the present disclosure that whether or not a dilator or sheath is needed will depend on the cavity to be accessed. For example, for cavities close to the skin, they may not be needed as a relevant incision may be performed close enough to the defect to be treated. However, for defects further inside the body, a needle and dilator may be used. For example, the device 100 may be configured to have a hollow channel extending along its entire length (e.g. through the porous medium 140/suction tube 130/inner tube 120). The channel may enable the device 100 to be railroaded over a guidewire and into the intended location in the body.

It will be appreciated that the systems and methods described above are specific examples, but that these examples are not to be considered limiting. Features described may not necessarily be essential, and systems and methods of the present disclosure may be provided without these features. Likewise, additional and/or alternative features may be provided. For example, it is to be appreciated that while the suction element has been described as a suction tube 130 connected to an inner tube 120 at a connection, this could be provided by one suction tube 130 or inner tube 120 (e.g. which extends from outside the patient to inside the patient). Likewise, the connection 125 described between the inner tube 120 and the suction tube 130 need not be a threaded connection using the coil wire. The inner tube 120 may not even be a coil wire, it may be a tube (e.g. which has, or does not have, fenestrations therein). The connection may be provided using adhesive or an additional component for attaching the two features together. Also, it is to be appreciated that in some examples, the porous medium 140 may have a shape selected to increase flexibility and compression of the porous medium 140 without having a suction tube 130 with fenestrations 135.

It is to be appreciated in the context of the present disclosure that examples of methods disclosed herein may be applied to a human or animal body without providing any surgical or therapeutic effect. For instance, it will be appreciated that such methods may be applied ex vivo, and/or to tissue samples that are not part of the living human or animal body. For example, the methods described herein may be practiced on meat, tissue samples, cadavers, and other non-living objects.

It will be appreciated from the discussion above that the examples shown in the figures are merely exemplary, and include features which may be generalised, removed or replaced as described herein and as set out in the claims. As will be appreciated by the skilled reader in the context of the present disclosure, each of the examples described herein may be implemented in a variety of different ways. Any feature of any aspects of the disclosure may be combined with any of the other aspects of the disclosure. For example method aspects may be combined with apparatus aspects, and features described with reference to the operation of particular elements of apparatus may be provided in methods which do not use those particular types of apparatus. In addition, each of the features of each of the examples is intended to be separable from the features which it is described in combination with, unless it is expressly stated that some other feature is essential to its operation. Each of these separable features may of course be combined with any of the other features of the examples in which it is described, or with any of the other features or combination of features of any of the other examples described herein. Furthermore, equivalents and modifications not described above may also be employed without departing from the invention.

Other examples and variations of the disclosure will be apparent to the skilled addressee in the context of the present disclosure.

The invention claimed is:

1. A vacuum therapy device for treatment of a defect internal of a human or animal body, the device comprising:
- a porous medium for treatment of the defect;
- a catheter having a proximal end and a distal end, wherein the catheter is configured to be inserted into the body to enable deployment of the porous medium through an opening at the distal end for treatment of the defect; and
- a suction element within the catheter, the suction element comprising a suction tube connected to the porous medium to provide suction thereat;
- wherein the porous medium is movable between: (i) a proximal position in which a majority of the porous medium is inside the catheter for insertion of the catheter and the porous medium into the body, and (ii) a distal position in which a portion of the porous medium is located outside the catheter for treatment of the defect;
- wherein a cross-section of the shape of the porous medium includes one or more spokes extending radially outward, wherein two adjacent spokes are separated by a separation region, wherein the separation region is more flexible and/or compressible than the spokes.

2. The device of claim 1, wherein each spoke is tapered so that each spoke is narrower at its most radially outward point than a more radially inward point.

3. The device of claim 1, wherein each spoke has a rounded tip.

4. The device of claim 1, wherein the separation region comprises at least one of: (i) less dense porous medium, and (ii) no porous medium.

5. The device of claim 1, wherein the separation region is larger than a pore size of the porous medium.

6. The device of claim 1, wherein the porous medium includes one or more compression segments comprising less dense and/or no porous medium.

7. The device of claim 6, wherein said compression segments are at least partially surrounded by porous medium.

8. The device of claim 7, wherein the compression segments are encompassed within an outer perimeter of the porous medium.

9. The device of claim 1, wherein a transverse cross-section of the shape of the porous medium is at least one of: (i) non-circular, or (ii) includes one or more cutaway portions without porous medium.

10. The device of claim 1, wherein a hollow passageway extends through a portion of the porous medium, and wherein the suction tube is at least partially within the hollow passageway.

11. The device of claim 10, wherein the suction tube has a plurality of fenestrations therein.

12. The device of claim 11, wherein the fenestrations extend along the portion of the suction tube within the hollow passageway of the porous medium.

13. The device of claim 10, wherein the hollow passageway comprises a hollow core extending along a central axis of the porous medium.

14. The device of claim 1, wherein the suction element comprises an inner tube for connecting the suction tube to a source for providing negative pressure.

15. The device of claim 14, wherein the catheter comprises an inner lining and/or coating arranged to inhibit friction between the catheter and the inner tube.

16. The device of claim 1, wherein the catheter is arranged to define an internal ledge near the distal end of the catheter where the internal diameter of the catheter transitions from a larger diameter to a smaller diameter.

17. The device of claim 16, wherein the ledge is at a distance from the distal end of the catheter selected based on a length of the porous medium.

18. The device of claim 17, wherein the length is selected so that the porous medium will abut the ledge with a volume of porous medium extending out of the distal end of the catheter for providing a soft leading edge of the catheter during insertion into the body.

* * * * *